US012778766B2

(12) United States Patent
McLaughlin

(10) Patent No.: US 12,778,766 B2
(45) **Date of Patent: *Nov. 3, 2026**

(54) EXPANDABLE INTERVERTEBRAL IMPLANT AND INSTRUMENTS FOR INSTALLING THE SAME

(71) Applicant: GLOBUS MEDICAL, INC., Audubon, PA (US)

(72) Inventor: Colm McLaughlin, Glenside, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/022,286

(22) Filed: Jan. 15, 2025

(65) Prior Publication Data

US 2025/0152376 A1 May 15, 2025

Related U.S. Application Data

(63) Continuation of application No. 16/535,142, filed on Aug. 8, 2019, now Pat. No. 12,208,017, which is a
(Continued)

(51) Int. Cl.
*A61F 2/46* (2006.01)
*A61B 17/86* (2006.01)
(Continued)

(52) U.S. Cl.
CPC ............ *A61F 2/4425* (2013.01); *A61B 17/86* (2013.01); *A61F 2/30749* (2013.01); *A61F 2/4455* (2013.01); *A61F 2/447* (2013.01); *A61F 2002/30261* (2013.01); *A61F 2002/30266* (2013.01); *A61F 2002/30329* (2013.01);
(Continued)

(58) Field of Classification Search
CPC ................................ A61F 2/46; A61F 2/4611
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Anu Ramana

(57) ABSTRACT

An implant including first and second end plates, each of which defines at least one anterior ramped surface and at least one posterior ramped surface. A posterior actuator is positioned between the first and second end plates and has guiding ramp surfaces which correspond with the posterior ramped surfaces. An anterior actuator is positioned between the first and second end plates and guiding ramp surfaces which correspond with the anterior ramped surfaces. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

20 Claims, 22 Drawing Sheets

Related U.S. Application Data continuation-in-part of application No. 16/116,396, filed on Aug. 29, 2018, now Pat. No. 10,722,379, which is a continuation-in-part of application No. 15/808,180, filed on Nov. 9, 2017, now Pat. No. 10,709,569.

(51) Int. Cl.
*A61F 2/30* (2006.01)
*A61F 2/44* (2006.01)

(52) U.S. Cl.
CPC ............... *A61F 2002/30331* (2013.01); *A61F 2002/30365* (2013.01); *A61F 2002/30367* (2013.01); *A61F 2002/30405* (2013.01); *A61F 2002/30411* (2013.01); *A61F 2002/30433* (2013.01); *A61F 2002/30471* (2013.01); *A61F 2002/30507* (2013.01); *A61F 2002/30523* (2013.01); *A61F 2002/30537* (2013.01); *A61F 2002/30538* (2013.01); *A61F 2002/30556* (2013.01); *A61F 2002/30579* (2013.01); *A61F 2002/30593* (2013.01); *A61F 2002/30622* (2013.01); *A61F 2002/30624* (2013.01); *A61F 2/442* (2013.01); *A61F 2002/443* (2013.01); *A61F 2/4603* (2013.01); *A61F 2/4611* (2013.01); *A61F 2002/4625* (2013.01); *A61F 2002/4627* (2013.01)

(56) References Cited

U.S. PATENT DOCUMENTS 4,863,476 A 9/1989 Shepperd
4,863,477 A 9/1989 Monson
5,123,926 A 6/1992 Pisharodi
5,290,312 A 3/1994 Kojimoto et al.
5,306,310 A 4/1994 Siebels
5,375,823 A 12/1994 Navas
5,390,683 A 2/1995 Pisharodi
5,522,899 A 6/1996 Michelson
5,534,030 A 7/1996 Navarro et al.
5,554,191 A 9/1996 Lahille et al.
5,571,192 A 11/1996 Schonhoffer
5,645,596 A 7/1997 Kim
5,653,763 A 8/1997 Errico et al.
5,665,122 A 9/1997 Kambin
5,676,701 A 10/1997 Yuan et al.
6,039,761 A 3/2000 Li et al.
6,045,579 A 4/2000 Hochschuler et al.
6,080,193 A 6/2000 Hochschuler et al.
6,099,531 A 8/2000 Bonutti
6,126,689 A 10/2000 Brett
6,176,882 B1 1/2001 Biedermann et al.
6,258,125 B1 7/2001 Paul et al.
6,554,863 B2 4/2003 Paul et al.
6,558,423 B1 5/2003 Michelson
6,562,074 B2 5/2003 Gerbec et al.
6,576,016 B1 6/2003 Hochschuler et al.
6,641,614 B1 11/2003 Wagner et al.
6,648,917 B2 11/2003 Gerbec et al.
6,666,891 B2 12/2003 Boehm, Jr. et al.
6,692,495 B1 2/2004 Zacouto
6,706,070 B1 3/2004 Wagner et al.
6,752,832 B2 6/2004 Ulrich
6,814,756 B1 11/2004 Michelson
6,830,570 B1 * 12/2004 Frey .................. A61B 17/1642 623/17.16
6,830,589 B2 12/2004 Erickson
6,849,093 B2 2/2005 Michelson
6,852,129 B2 2/2005 Gerbec et al.
6,863,673 B2 3/2005 Gerbec et al.
6,881,228 B2 4/2005 Zdeblick et al.
7,018,415 B1 3/2006 McKay
7,070,598 B2 7/2006 Lim et al.
7,204,853 B2 4/2007 Gordon
7,217,291 B2 5/2007 Zucherman et al.
7,282,063 B2 10/2007 Cohen et al.
7,316,714 B2 1/2008 Gordon
7,473,276 B2 1/2009 Aebi et al.
7,547,325 B2 6/2009 Biedermann et al.
7,604,643 B2 * 10/2009 Ciccone ............... A61B 17/888 606/104
7,621,953 B2 11/2009 Braddock, Jr. et al.
7,632,281 B2 * 12/2009 Errico .................. A61F 2/4611 606/99
7,641,693 B2 1/2010 Gutlin et al.
7,682,396 B2 3/2010 Beaurain et al.
7,749,270 B2 7/2010 Peterman
7,753,958 B2 7/2010 Gordon
7,771,473 B2 8/2010 Thramann
7,780,732 B2 8/2010 Abernathie
7,799,081 B2 9/2010 McKinley
7,815,683 B2 10/2010 Melkent et al.
7,837,734 B2 11/2010 Zucherman et al.
7,875,078 B2 1/2011 Wysocki et al.
7,901,409 B2 3/2011 Canaveral et al.
7,909,869 B2 3/2011 Gordon
7,951,199 B2 5/2011 Miller
7,985,256 B2 7/2011 Grotz et al.
8,062,375 B2 11/2011 Glerum
8,070,813 B2 12/2011 Grotz et al.
8,123,810 B2 2/2012 Gordon
8,137,405 B2 3/2012 Kostuik et al.
8,192,495 B2 6/2012 Simpson et al.
8,303,663 B2 11/2012 Jimenez et al.
8,377,140 B2 2/2013 DeFalco et al.
8,394,129 B2 3/2013 Lopez et al.
8,394,143 B2 3/2013 Grotz et al.
8,419,743 B2 * 4/2013 Smith .................. A61F 2/4611 623/22.12
8,435,296 B2 5/2013 Kadaba et al.
8,454,695 B2 6/2013 Grotz et al.
8,647,386 B2 2/2014 Gordon
8,696,751 B2 4/2014 Ashley et al.
8,771,360 B2 7/2014 Jimenez et al.
8,894,710 B2 11/2014 Simpson et al.
8,932,355 B2 1/2015 Grotz et al.
8,940,049 B1 1/2015 Jimenez et al.
8,956,413 B2 2/2015 Ashley et al.
8,992,620 B2 3/2015 Ashley et al.
9,028,550 B2 5/2015 Shulock et al.
9,226,836 B2 * 1/2016 Glerum .................. A61F 2/447
9,314,287 B2 * 4/2016 Smith .................. A61F 2/4637
9,358,125 B2 6/2016 Jimenez et al.
9,532,883 B2 1/2017 McLuen et al.
9,572,685 B2 * 2/2017 Perry .................... A61F 2/4611
9,622,878 B2 4/2017 Grotz
9,907,582 B1 * 3/2018 Olea .................. A61B 17/7079
9,987,149 B2 * 6/2018 Simpson ............... A61F 2/4611
10,390,967 B2 * 8/2019 Livorsi .............. A61B 17/8875
12,290,287 B2 * 5/2025 Slover ................ A61B 17/7065
2002/0045945 A1 4/2002 Liu et al.
2002/0068976 A1 6/2002 Jackson
2002/0068977 A1 6/2002 Jackson
2003/0176926 A1 9/2003 Boehm et al.
2004/0030387 A1 2/2004 Landry et al.
2004/0049271 A1 3/2004 Biedermann et al.
2004/0054412 A1 3/2004 Gerbec et al.
2004/0087947 A1 5/2004 Lim et al.
2004/0153065 A1 8/2004 Lim
2005/0021041 A1 1/2005 Michelson
2005/0021145 A1 1/2005 de Villiers et al.
2005/0033432 A1 2/2005 Gordon et al.
2005/0080422 A1 4/2005 Otte et al.
2005/0113916 A1 5/2005 Branch
2005/0149188 A1 7/2005 Cook et al.
2005/0171541 A1 8/2005 Boehm
2005/0251258 A1 11/2005 Jackson
2005/0273171 A1 12/2005 Gordon
2005/0273174 A1 12/2005 Gordon
2005/0278026 A1 12/2005 Gordon
2005/0283244 A1 12/2005 Gordon
2005/0283245 A1 12/2005 Gordon

(56) References Cited

U.S. PATENT DOCUMENTS

| | | | |
|---|---|---|---|
| 2006/0004453 | A1 | 1/2006 | Bartish, Jr. et al. |
| 2006/0015184 | A1 | 1/2006 | Winterbottom et al. |
| 2006/0058878 | A1 | 3/2006 | Michelson |
| 2006/0084986 | A1 | 4/2006 | Grinberg et al. |
| 2006/0122701 | A1 | 6/2006 | Kister |
| 2006/0129244 | A1 | 6/2006 | Ensign |
| 2006/0142859 | A1 | 6/2006 | Mcluen |
| 2006/0149385 | A1 | 7/2006 | Mckay |
| 2006/0195192 | A1 | 8/2006 | Gordon et al. |
| 2006/0229729 | A1 | 10/2006 | Gordon |
| 2006/0241770 | A1 | 10/2006 | Rhoda et al. |
| 2006/0253201 | A1 | 11/2006 | Mcluen |
| 2007/0043442 | A1 | 2/2007 | Abernathie |
| 2007/0050030 | A1 | 3/2007 | Kim |
| 2007/0050032 | A1 | 3/2007 | Gittings et al. |
| 2007/0055377 | A1 | 3/2007 | Hanson et al. |
| 2007/0191951 | A1 | 8/2007 | Branch |
| 2007/0255415 | A1 | 11/2007 | Edie et al. |
| 2007/0270963 | A1 | 11/2007 | Melkent et al. |
| 2007/0270968 | A1 | 11/2007 | Baynham |
| 2008/0021559 | A1 | 1/2008 | Thramann |
| 2008/0065222 | A1 | 3/2008 | Hamada |
| 2008/0114467 | A1 | 5/2008 | Capote et al. |
| 2008/0140207 | A1 | 6/2008 | Olmos et al. |
| 2008/0147194 | A1 | 6/2008 | Grotz et al. |
| 2008/0161933 | A1 | 7/2008 | Grotz et al. |
| 2008/0167657 | A1 | 7/2008 | Greenhalgh |
| 2008/0183204 | A1 | 7/2008 | Greenhalgh et al. |
| 2008/0221694 | A1 | 9/2008 | Warnick et al. |
| 2008/0275455 | A1 | 11/2008 | Berry et al. |
| 2008/0281346 | A1 | 11/2008 | Greenhalgh et al. |
| 2008/0288073 | A1 | 11/2008 | Renganath et al. |
| 2008/0300598 | A1 | 12/2008 | Barreiro et al. |
| 2008/0306488 | A1 | 12/2008 | Altarac et al. |
| 2008/0319487 | A1 | 12/2008 | Fielding et al. |
| 2008/0319549 | A1 | 12/2008 | Greenhalgh et al. |
| 2009/0024217 | A1 | 1/2009 | Levy et al. |
| 2009/0062833 | A1 | 3/2009 | Song |
| 2009/0076616 | A1 | 3/2009 | Duggal et al. |
| 2009/0125062 | A1 | 5/2009 | Arnin |
| 2009/0149956 | A1 | 6/2009 | Greenhalgh et al. |
| 2009/0149959 | A1 | 6/2009 | Conner et al. |
| 2009/0204218 | A1 | 8/2009 | Richelsoph |
| 2009/0222100 | A1 | 9/2009 | Cipoletti et al. |
| 2009/0240334 | A1 | 9/2009 | Richelsoph |
| 2009/0270989 | A1 | 10/2009 | Conner et al. |
| 2009/0281628 | A1 | 11/2009 | Oglaza et al. |
| 2009/0292361 | A1 | 11/2009 | Lopez |
| 2009/0299478 | A1 | 12/2009 | Carls et al. |
| 2009/0312763 | A1 | 12/2009 | McCormack |
| 2010/0049324 | A1 | 2/2010 | Valdevit |
| 2010/0070041 | A1 | 3/2010 | Peterman |
| 2010/0082109 | A1 | 4/2010 | Greenhalgh et al. |
| 2010/0145455 | A1 | 6/2010 | Simpson et al. |
| 2010/0179657 | A1 | 7/2010 | Greenhalgh et al. |
| 2010/0211176 | A1 | 8/2010 | Greenhalgh |
| 2010/0222816 | A1 | 9/2010 | Gabelberger et al. |
| 2010/0286783 | A1 | 11/2010 | Lechmann et al. |
| 2011/0035011 | A1 | 2/2011 | Cain |
| 2011/0093074 | A1 | 4/2011 | Glerum et al. |
| 2011/0160861 | A1 | 6/2011 | Jimenez et al. |
| 2011/0172774 | A1 | 7/2011 | Varela |
| 2011/0276142 | A1 | 11/2011 | Niemiec et al. |
| 2011/0301713 | A1 | 12/2011 | Theofilos |
| 2011/0319997 | A1 | 12/2011 | Glerum et al. |
| 2012/0035729 | A1 | 2/2012 | Glerum et al. |
| 2012/0059470 | A1 | 3/2012 | Weiman |
| 2012/0059472 | A1 | 3/2012 | Weiman |
| 2012/0109308 | A1 | 5/2012 | Lechmann et al. |
| 2012/0130496 | A1 | 5/2012 | Duffield et al. |
| 2012/0165945 | A1 | 6/2012 | Hansell et al. |
| 2012/0185049 | A1 | 7/2012 | Varela |
| 2012/0209386 | A1 | 8/2012 | Triplett et al. |
| 2012/0215313 | A1 | 8/2012 | Saidha et al. |
| 2012/0226357 | A1 | 9/2012 | Varela |
| 2012/0265309 | A1 | 10/2012 | Glerum et al. |
| 2012/0277861 | A1 | 11/2012 | Steele et al. |
| 2012/0277870 | A1 | 11/2012 | Wolters et al. |
| 2012/0323329 | A1 | 12/2012 | Jimenez et al. |
| 2012/0330426 | A1 | 12/2012 | Mclaughlin et al. |
| 2013/0023993 | A1 | 1/2013 | Weiman |
| 2013/0023994 | A1 | 1/2013 | Glerum |
| 2013/0158663 | A1 | 6/2013 | Miller et al. |
| 2013/0158669 | A1 | 6/2013 | Sungarian et al. |
| 2013/0197647 | A1 | 8/2013 | Wolters et al. |
| 2013/0211526 | A1 | 8/2013 | Alheidt et al. |
| 2013/0274883 | A1 | 10/2013 | McLuen et al. |
| 2014/0067071 | A1 | 3/2014 | Weiman et al. |
| 2014/0088714 | A1 | 3/2014 | Miller et al. |
| 2014/0163683 | A1 | 6/2014 | Seifert et al. |
| 2015/0066145 | A1 | 3/2015 | Rogers et al. |
| 2015/0088258 | A1 | 3/2015 | Jimenez et al. |
| 2015/0134064 | A1 | 5/2015 | Grotz et al. |
| 2015/0216676 | A1 | 8/2015 | Shulock et al. |
| 2015/0289988 | A1 | 10/2015 | Ashley et al. |
| 2015/0374508 | A1 | 12/2015 | Sandul |
| 2016/0166396 | A1 | 6/2016 | McClintock |
| 2016/0324654 | A1 | 11/2016 | Loebl et al. |
| 2017/0100258 | A1 | 4/2017 | Jimenez et al. |
| 2017/0119543 | A1 | 5/2017 | Dietzel et al. |

FOREIGN PATENT DOCUMENTS

| | | | |
|---|---|---|---|
| DE | 4327054 | C1 | 4/1995 |
| EP | 0576379 | B1 | 6/1993 |
| EP | 0610837 | B1 | 7/1994 |
| EP | 3111896 | A1 | 1/2017 |
| FR | 2794968 | A1 | 12/2000 |
| JP | 2000-513263 | A | 10/2000 |
| KR | 200290058 | Y1 | 9/2002 |
| SU | 1424826 | A1 | 9/1988 |
| WO | 9201428 | A1 | 2/1992 |
| WO | 9525485 | A1 | 9/1995 |
| WO | 1999042062 | A1 | 8/1999 |
| WO | 1999066867 | A1 | 12/1999 |
| WO | 2002045625 | A1 | 6/2002 |
| WO | 2004019829 | A1 | 3/2004 |
| WO | 2004069033 | A2 | 8/2004 |
| WO | 2006045094 | A2 | 4/2006 |
| WO | 2006047587 | A2 | 5/2006 |
| WO | 2006113080 | A2 | 10/2006 |
| WO | 2008044057 | A1 | 4/2008 |
| WO | 2008134515 | A1 | 11/2008 |
| WO | 2009114381 | A1 | 9/2009 |
| WO | 2010103344 | A1 | 9/2010 |
| WO | 2012031267 | A1 | 3/2012 |
| WO | 2015009793 | A1 | 1/2015 |

* cited by examiner

EXPANDABLE INTERVERTEBRAL IMPLANT AND INSTRUMENTS FOR INSTALLING THE SAME

CROSS REFERENCE TO RELATED APPLICATIONS

This application is a continuation of U.S. patent application Ser. No. 16/535,142, filed on Aug. 8, 2019 now U.S. Pat. No. 12,208,017, which is a continuation-in-part of U.S. patent application Ser. No. 16/116,396, filed on Aug. 29, 2018, now U.S. Pat. No. 10,722,379, which is a continuation-in-part of U.S. patent application Ser. No. 15/808,180, filed on Nov. 9, 2017, now U.S. Pat. No. 10,709,569, the contents of each of which is incorporated by reference herein in its entirety for all purposes.

FIELD OF THE INVENTION

This present disclosure relates to stabilizing adjacent vertebrae of the spine by inserting an intervertebral implant, and more particularly an intervertebral implant that is adjustable in height and/or angularity and associated methods.

BACKGROUND

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY

To meet this and other needs, expandable implants, systems, and methods are provided. The expandable implant may be expandable and adjustable in height and/or angularity. The implant may be inserted into an intervertebral disc space at a minimized height, and then expanded axially to restore height loss in the disc space. The implant may provide distraction as well as achieving optimal height restoration. The implant may also change in lordotic angulation independently from its expansion. This independent expansion and lordotic angulation may solve some of the problems currently encountered, such as excessive impaction during insertion, visual obstruction, and imperfect matching with patient's lordosis due to discrete increments in lordotic angulation. It will be appreciated that although generally described with respect to lordotic angulation, the implant may also be configured to provide kyphotic expansion and angulation to treat kyphosis as well.

In at least one embodiment, the present disclosure provides an implant for therapeutically separating bones of a joint. The implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

In at least one embodiment, the present invention provides an implant including a first end plate extending between an anterior end and a posterior end. The first end plate defines at least one anterior ramped surface and at least one posterior ramped surface. A second end plate extends between an anterior end and a posterior end and defines at least one anterior ramped surface and at least one posterior ramped surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator. The actuator assembly includes an actuator screw extending between a posterior end and an anterior end with a first external thread set proximate the posterior end and a second external thread set proximate the anterior end wherein the first and second external thread sets are oppositely handed. The posterior end of the actuator screw extends through and threadably engages a through passage in the posterior actuator. The actuator assembly further includes an actuator nut extending between a posterior end and an anterior end with a through passage extending from the posterior end to the anterior end and defining an internal thread within the through passage. The internal thread is threadably engaged with the second set of external threads. The actuator nut extends through the anterior actuator such that the actuator nut is axially fixed relative to the anterior actuator but rotatable relative thereto. Rotation of the actuator screw while the actuator nut does not rotate causes the posterior actuator and the anterior actuator to move simultaneously, rotation of the actuator screw and the actuator nut together causes the posterior actuator to move independently of the anterior actuator, and rotation of the actuator nut while the actuator screw does not rotate causes the anterior actuator to move independently of the posterior actuator.

In at least one embodiment, the implant may include one or more bearings. The bearings may be configured to connect one or both of the end plates to the actuator assembly and allow the actuator screw to rotate regardless of end plate angulation. For example, the posterior end of the actuator screw may include a ball which is supported in a spherical bearing supported by the first and second end plates. In an alternative arrangement, the implant may be provided without bearings present, such that the end plates would be free to pivot or translate without restriction.

In at least one embodiment, the disclosure provides a method of fusing adjacent vertebral bodies including inserting an implant defining a longitudinal axis extending between distal and proximal ends between bones of the joint, the implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator. The method further includes actuating the actuator assembly after the implant is inserted to move the first and second end plates relative to one another to increase or decrease the lordotic angle or to move the first and second endplates farther apart to separate bones of the joint.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

Figure 1:
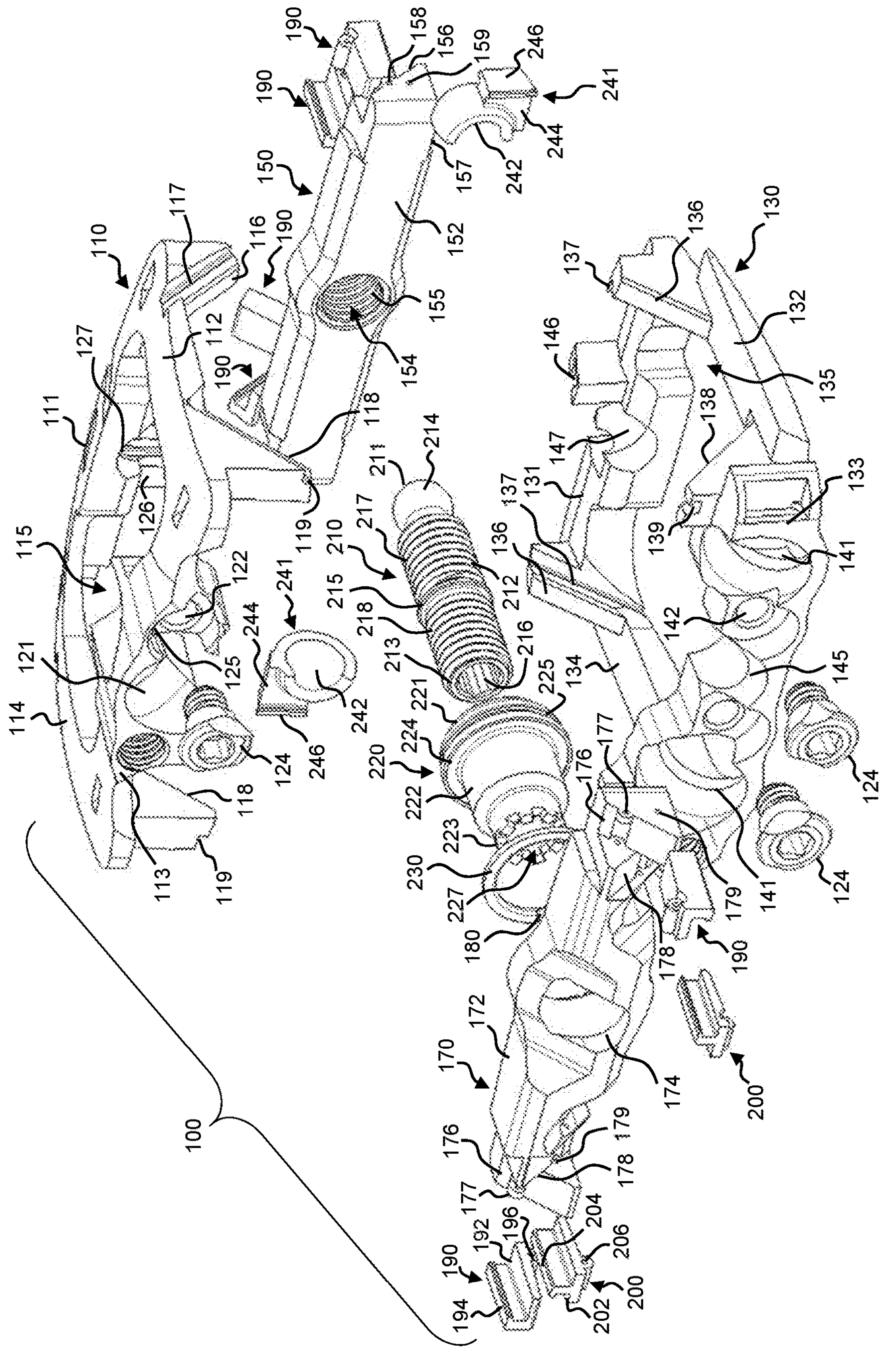
FIG. 1 is an exploded perspective view of an implant in accordance with an embodiment of the disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The terms “a” or “an”, as used herein, are defined as one or more than one. The term plurality, as used herein, is defined as two or more than two. The term another, as used herein, is defined as at least a second or more. The terms “including” and “having,” as used herein, are defined as comprising (i.e., open language).

Implants of the disclosure allow for insertion into the intervertebral disc space at a minimized height and then expansion axially to restore height loss in the disc space. Implants of the disclosure allow continuous expansion and retraction within a range of expansion as well as achieving optimal height restoration. Implants of the disclosure may also change in lordotic angulation independently from its expansion. Implants of the disclosure may be utilized to minimize impaction during insertion, visual obstruction, and imperfect matching with a patient’s lordosis due to discrete increments in lordotic angulation. Additionally, implants of the disclosure may also be collapsed and repositioned, as therapeutically indicated for the patient.

Referring to FIGS. 1-5 and 7-13, an implant 100 in accordance with an embodiment of the disclosure will be described. The implant 100 is operative, when positioned between adjacent bones of a joint, such as for example vertebrae (not shown), to stabilize a joint formed by adjacent vertebrae. The implant 100 is illustrated in an anterior interbody spacer configuration but it could also be used in other approaches, for example, such as direct lateral where coronal deformity is encountered.

Figure 2:
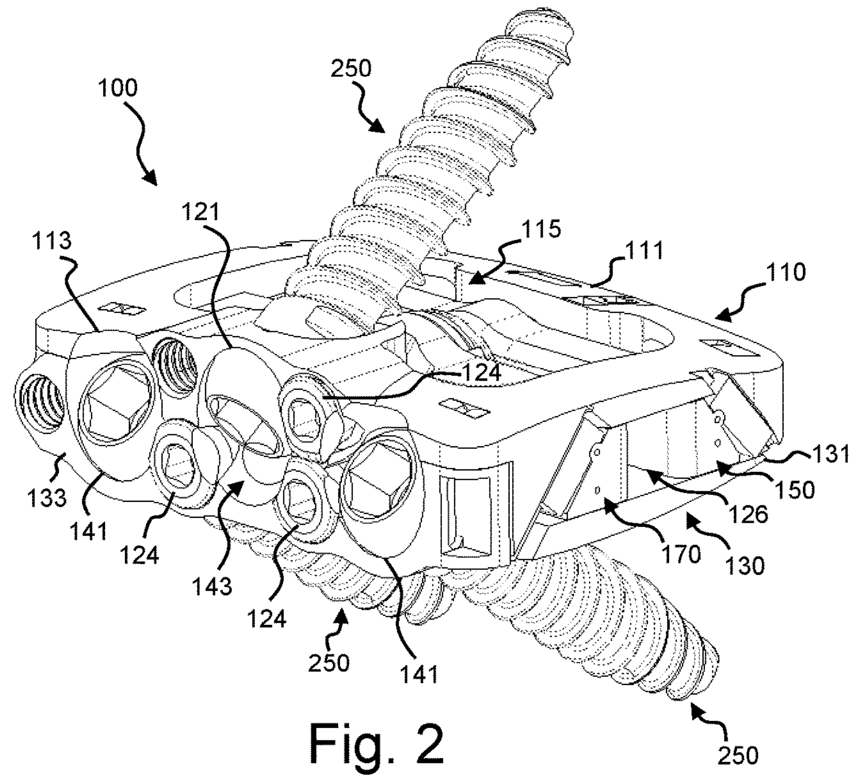
FIG. 2 is a perspective view of the implant of FIG. 1 in a compressed or reduced height configuration, together with three mounted bone screws.
Figure 3:
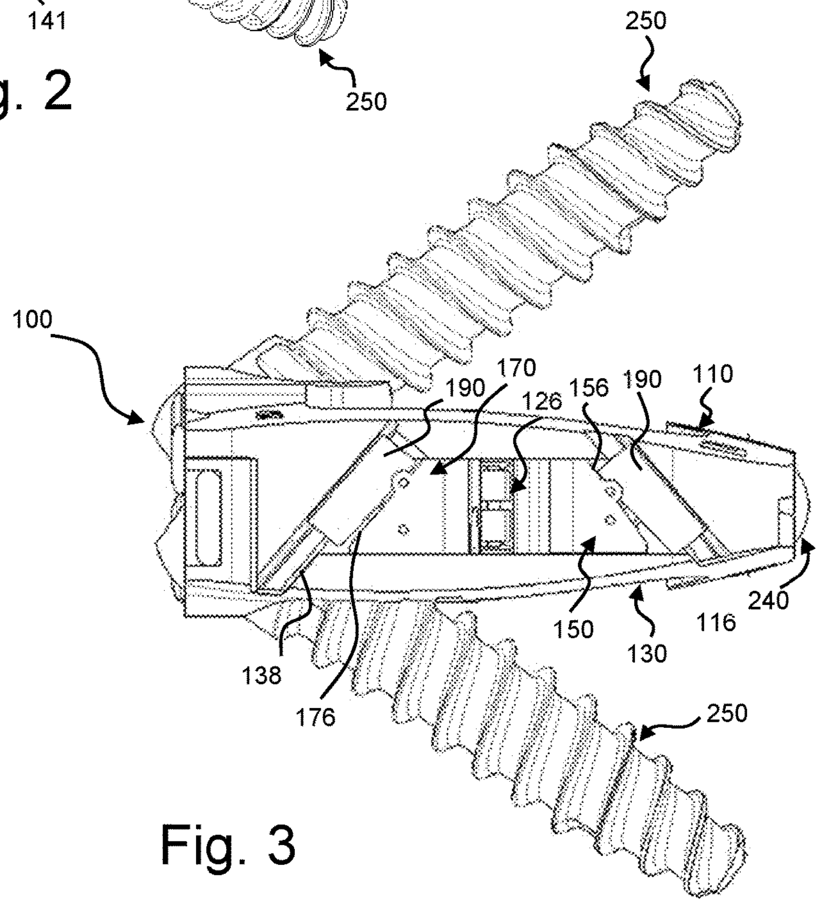
FIG. 3 is a side elevation view of the implant as shown in FIG. 2.

With reference to FIGS. 1-3, the implant 100 generally includes upper and lower endplates 110, 130, anterior and posterior actuators 150, 170, actuator pivot members 190, 200, an actuator screw 210, an actuator nut 220, a spherical bearing 240 and a thrust washer 230. In addition, the implant may include a plurality of blocking screws 124 on the endplates 110, 130 to prevent migration of the fixation screws or anchors.

The upper end plate 110 includes a posterior rail 111 and an anterior rail 113 extending between opposed side rails 112, 114. The rails 111-114 extend about a through passage 115 into a graft chamber 128 within the implant. The passage 115 allows graft material or other therapeutically beneficial material to packed into or grow into the graft chamber 128. The upper end plate 110 defines a posterior guide ramp 116 along each side rail 112, 114 and an anterior guide ramp 118 along each side rail 112, 114. Each posterior guide ramp 116 defines a groove 117 configured to receive a portion of a respective pivot member 190 and each anterior guide ramp 118 defines a groove 117 configured to receive a portion of a respective pivot member 190. As will be described hereinafter, the pivot members 190 are pivotally connected to respective actuators 150, 170 and slide along the respective ramp 116, 118 as the plates 110, 130 expand or contract.

The anterior rail 113 defines at least one bone screw/anchor through hole 121, with one such hole 121 shown in the illustrated embodiment. A blocking screw hole 122 is positioned next to the through hole 121 and is configured to receive a blocking screw 124 which may be utilized to maintain the bone screw 250 or bone anchor 260 in the through hole 121. It will be appreciated that the bone screw 250 and bone anchor 260 may be used interchangeably in the respective hole 121 and may also be substituted with any other suitable fasteners. The anterior rail 113 also defines a first hemispherical portion 125 of a driver opening 143 as shown in FIG. 2. The posterior rail 111 defines a first hemispherical portion 127 of a seat for the spherical bearing 240, as will be described hereinafter. A receiving slot 126 extends next to the hemispherical portion 127 and is configured to receive a flange 246 of one of the bearing members 241 that defines a portion of the spherical bearing 240.

The lower end plate 130 includes a posterior rail 131 and an anterior rail 133 extending between opposed side rails 132, 134. The rails 131-134 extend about a through passage 135 into the graft chamber 128 within the implant. The passage 135 again allows graft material or other therapeutically beneficial material to packed into or grow into the graft chamber 128. The lower end plate 130 defines a posterior guide ramp 136 along each side rail 132, 134 and an anterior guide ramp 138 along each side rail 132, 134. The guide ramps 136 and 138 are laterally inward of the ramps 116, 118 such that the ramps 116, 118 may overlap the ramps 136, 138. Each posterior guide ramp 136 defines a groove 137 configured to receive a portion of a respective pivot member 190 and each anterior guide ramp 138 defines a groove 137 configured to receive a portion of a respective pivot member 200. As will be described hereinafter, the pivot members 190, 200 are pivotally connected to respective actuators 150, 170 and slide along the respective ramp 136, 138 as the plates 110, 130 expand or contract.

The anterior rail 133 defines at least one bone screw/anchor through hole 141, with two such holes 141 shown in the illustrated embodiment. A blocking screw hole 142 is positioned next to each through hole 141 and is configured to receive a blocking screw 124 which may be utilized to maintain the bone screw 250 or bone anchor 260 in the through hole 141. It will be appreciated that the bone screw 250 and bone anchor 260 may be used interchangeably in the respective holes 141 and may also be substituted with any other suitable fasteners. The anterior rail 133 also defines the second hemispherical portion 145 of the driver opening 143 as shown in FIG. 2. The posterior rail 131 defines the second hemispherical portion 147 of the seat for the spherical bearing 240. A receiving slot 146 extends next to the hemispherical portion 127 and is configured to receive a flange 246 of the other of the bearing members 241 that defines another portion of the spherical bearing 240.

Although anterior rails 113, 133 are shown with through holes 121, 141 configured to receive respective fasteners, it will be appreciated by one skilled in the art that the bore holes or through holes 121, 141 may be present in any suitable number and configuration for fixation. In the alternative, the bore holes or through holes 121, 141 may be omitted to provide a standalone device.

Figure 6:
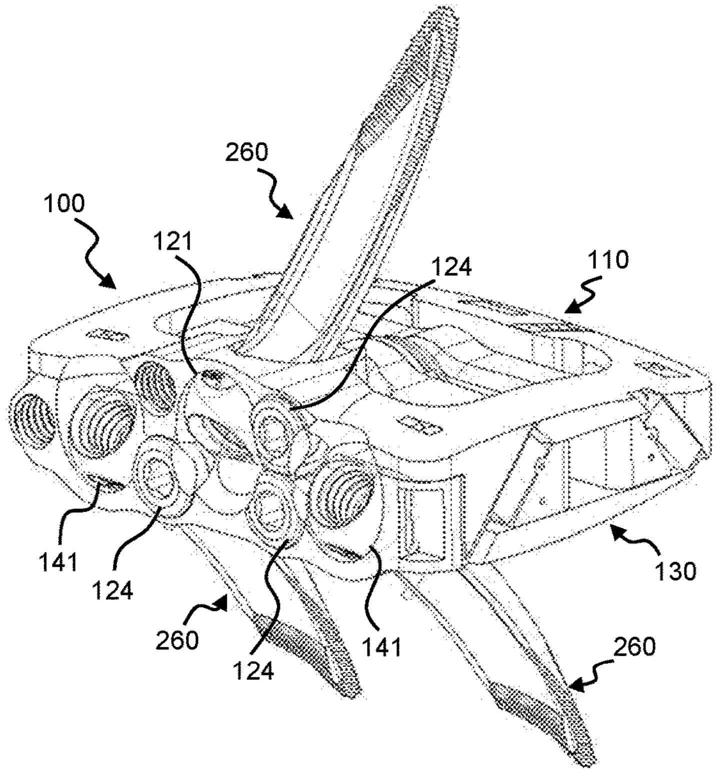
FIG. 6 is a perspective view of the implant of FIG. 1 in a compressed or reduced height configuration, together with three mounted bone anchors.
Figure 7:
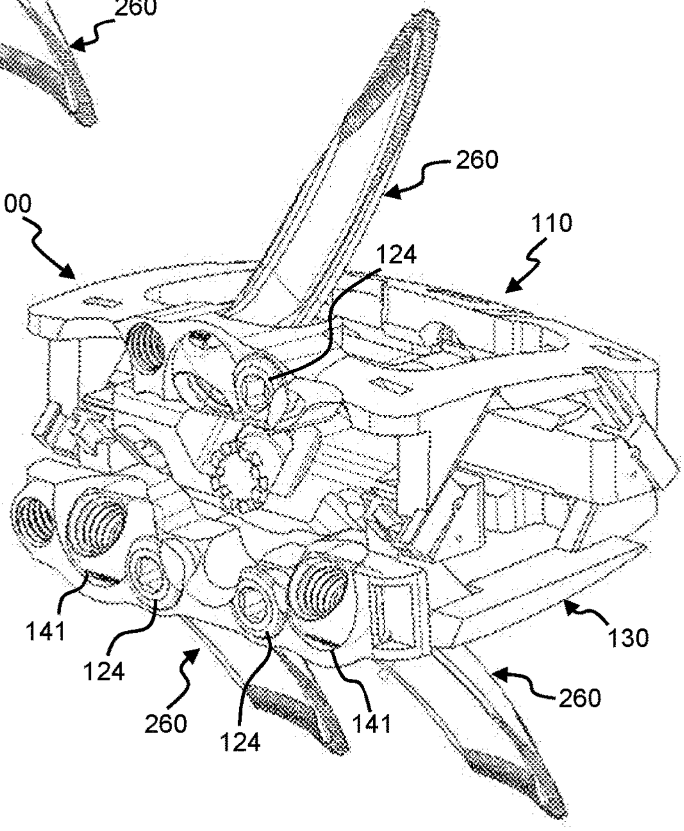
FIG. 7 is a perspective view of the implant of FIG. 1 in an expanded or increased height configuration, together with three mounted bone anchors.

While not shown, one or both of the end plates 110, 130 can be provided with teeth or other projections which can penetrate body tissue to reduce a likelihood of migration of implant 100 after implantation. Additionally, one or both of the end plates 110, 130 may be coated with or impregnated with therapeutic agents, including bone growth, healing, antimicrobial, or drug materials, which may be released at a therapeutic rate, using methods known to those skilled in the art. Additionally, while FIGS. 2-5 show bone screws 260 extending through the through holes 121, 141 for securing of the implant 100, the disclosure is not limited to such. For example, FIGS. 6 and 7 illustrate bone anchors 260 extending through the through holes 121, 141. Other anchoring elements may also be utilized. In each case, the through holes 121, 141 may have a concave opening such that the screws 250 or anchors 260 may be inserted into body tissue at an optimal angle with respect to implant 100, whereby optimal purchase may be obtained, or certain body tissue may be avoided.

Figure 4:
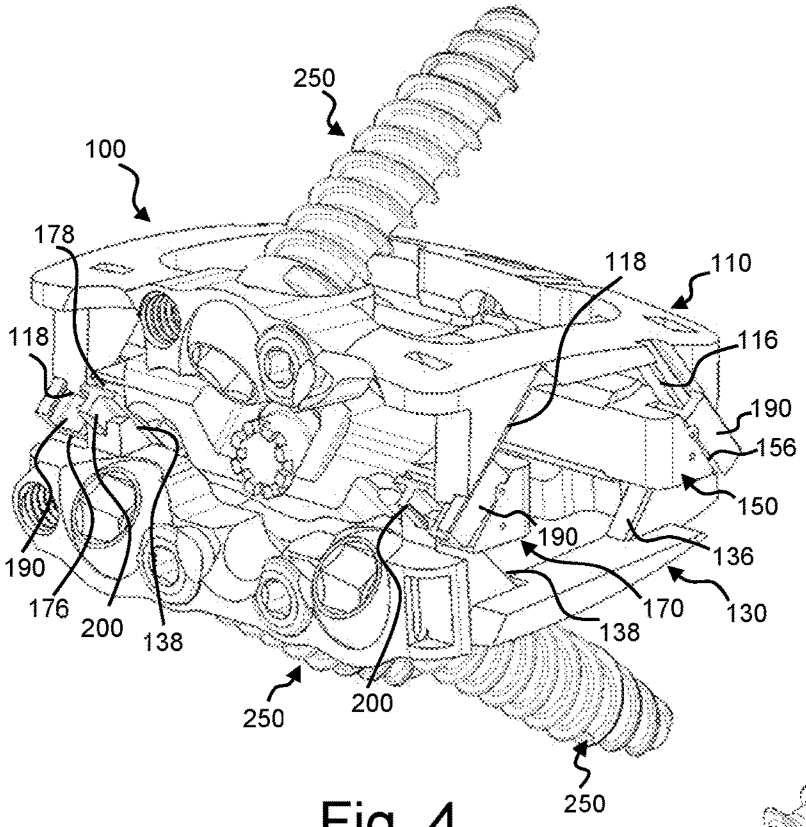
FIG. 4 is a perspective view of the implant of FIG. 1 in an expanded or increased height configuration, together with three mounted bone screws.
Figure 5:
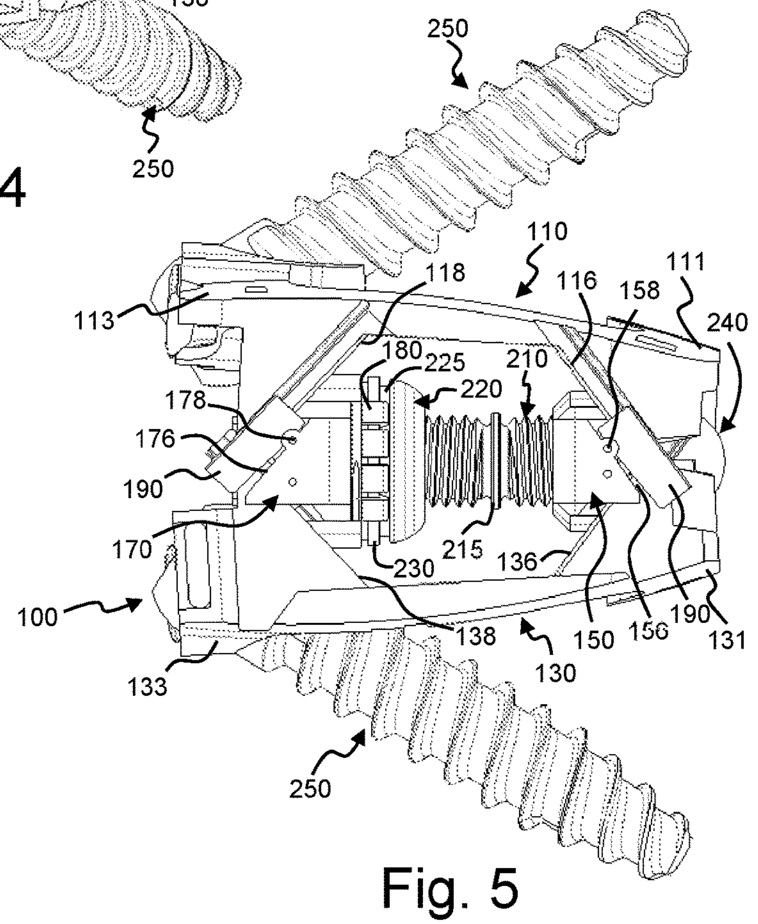
FIG. 5 is a side elevation view of the implant as shown in FIG. 4.

Implant 100 has a collapsed state or height, illustrated in FIGS. 2 and 3, and an expanded state or height, illustrated in FIGS. 4 and 5. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed state, implants 100 reduce impaction to tissue in the joint space during insertion, and form the least visually blocking or obstructing profile. Additionally, the lordotic angle of implant 100 may be adjusted to have an increased lordotic angle, illustrated in FIGS. 8 and 9, or a decreased lordotic angle, illustrated in FIGS. 10 and 11.

The anterior and posterior actuators 150, 170 are positioned between the plates 110, 130 and are moveable relative to the plates 110, 130 to control the separation between the plates 110, 130. The anterior actuator 150 is positioned between the plates 110, 130 proximate the anterior rails 111, 131. The anterior actuator 150 has a laterally extending body 152 with a central through passage 154 with internal threads 155 configured to threadably engage the actuator screw 210, as will be described hereinafter. An upper plate guiding ramp 156 is defined at each end of the body 152 and is configured to align with a respective anterior ramp 116 of the upper plate 110. Each of the upper plate guiding ramps 156 extends at the same incline angle as the opposing anterior ramp 116. Similarly, a lower plate guiding ramp 157 is defined inward of each end of the body 152 and is configured to align with a respective anterior ramp 136 of the lower plate 130. Each of the lower plate guiding ramps 157 extends at the same incline angle as the opposing anterior ramp 136. The body 152 defines pivot pin holes 158, 159 next to the guiding ramps 156, 157, respectively, for pivotal mounting of the pivot members 190.

The posterior actuator 170 is positioned between the plates 110, 130 proximate the posterior rails 113, 133. The anterior actuator 170 has a laterally extending body 172 with a central non-threaded through passage 174 configured to receive the actuator nut 220. A series of fingers 180 extend from the posterior side of the body 172 about the through passage 174 and are configured to engage and retain the actuator nut 220, as will be described hereinafter. An upper plate guiding ramp 176 is defined at each end of the body 172 and is configured to align with a respective posterior ramp 118 of the upper plate 110. Each of the upper plate guiding ramps 176 extends at the same incline angle as the opposing superior ramp 118. Similarly, a lower plate guiding ramp 177 is defined inward of each end of the body 172 and is configured to align with a respective superior ramp 138 of the lower plate 130. Each of the lower plate guiding ramps 177 extends at the same incline angle as the opposing superior ramp 138. The body 172 defines pivot pin holes 178, 179 next to the guiding ramps 176, 177, respectively, for pivotal mounting of the pivot members 190, 200.

Referring to FIG. 1, each of the pivot members 190 includes a guide surface 192 configured to engage and slide along a respective ramp 116, 118, 136. A groove engaging flange 194 extends from each guide surface 192 and is configured to engage within the respective ramp groove 117, 119, 137 to prevent separation from the respective ramp 116, 118, 136. The opposite side of each guide surface 192 defines a pivot slot 196 configured to align with respective pivot pin holes 158, 159, 178 such that a pivot pin (not shown) pivotally connects each pivot member 190 to a respective actuator 150, 170. The pivot members 200 are similar to the pivot members 190 and includes a guide surface 202 configured to engage and slide along a respective ramp 138. A groove engaging flange 204 extends from each guide surface 202, more centrally compared to the pivot member 190, and is configured to engage within the respective ramp groove 139 to prevent separation from the respective ramp 138. The opposite side of each guide surface 202 defines a pivot slot 206 configured to align with respective pivot pin holes 179 such that a pivot pin (not shown) pivotally connects each pivot member 200 to a respective actuator 170.

Figure 14:
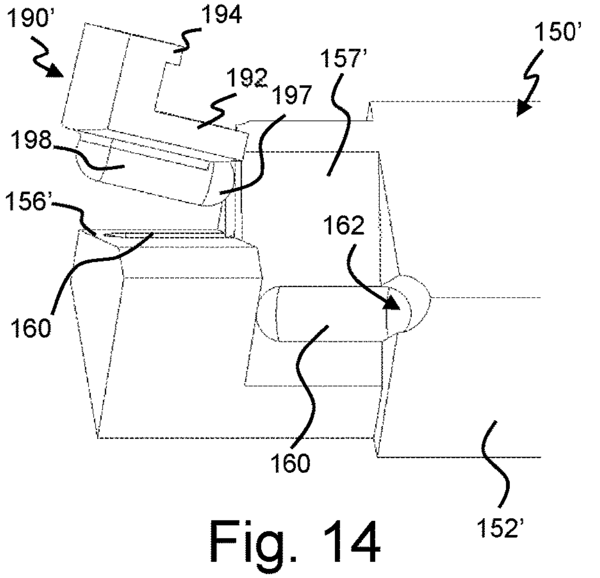
FIGS. 14-16 are expanded perspective views of a portion of an alternative actuator showing the sequential mounting of an alternative pivot member relative thereto.
Figure 15:
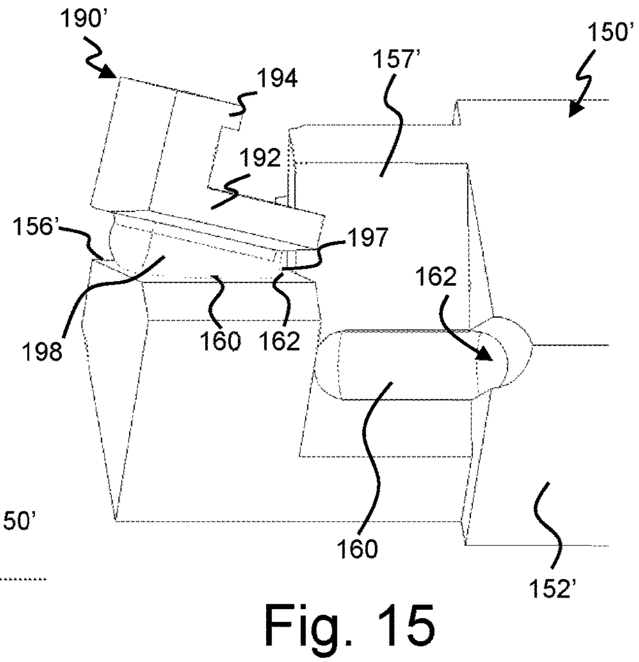
Figure 16:
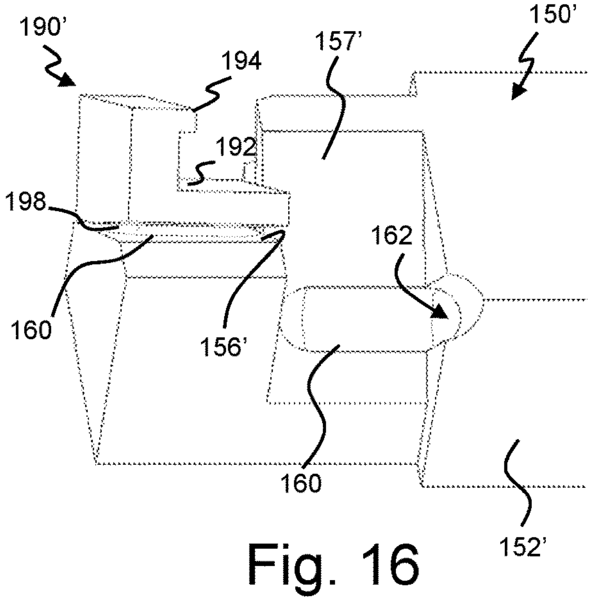
Figure 17:
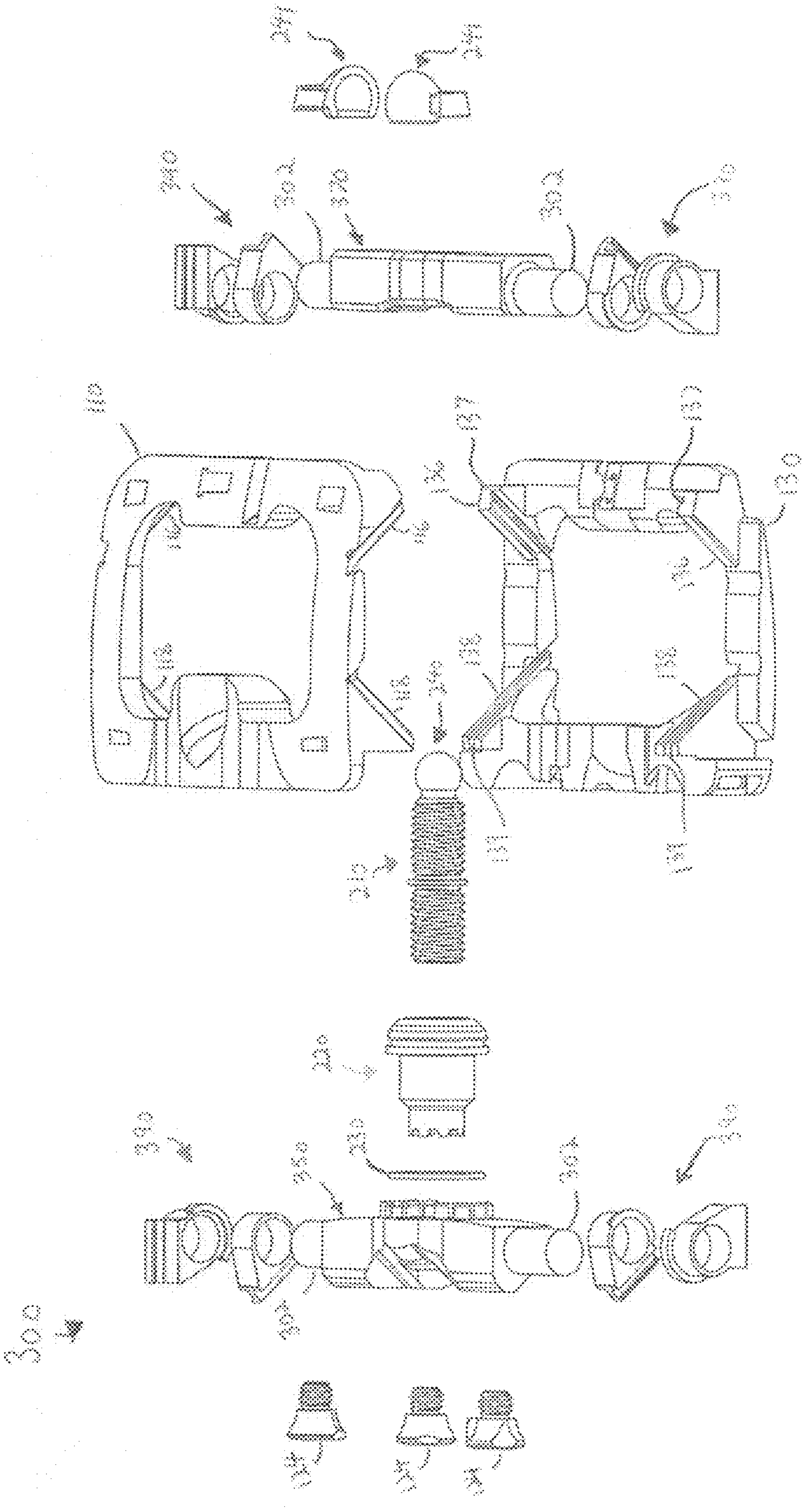
FIG. 17 is an exploded perspective view of an implant in accordance with an embodiment of the disclosure.

Referring to FIGS. 14-16, an alternative method of pivotally connecting the pivot members to the actuators will be described. While the figures show a posterior actuator 150', a similar construction may be provided for the anterior actuator. In the present embodiment, each of the ramps 156, 157 defines a pivot slot 160 with a portion 162 that extends laterally under a portion of the actuator body 152'. Instead of a pivot pin slot, each pivot member 190' has a rounded underside member 198 with an extending portion 197. The rounded underside member 198 fits into the pivot slot 160 with the extending portion 197 fitting into the portion 162 that extends laterally under a portion of the actuator body 152'. When fully placed as illustrated in FIG. 16, the pivot member 190' is retained in the actuator and is pivotal thereto.

The pivot members 190, 200 are pivotally connected to and thereby move with the respective actuator 150, 170 while also being engaged with the grooves 117, 119, 137, 139 in the upper and lower end plates 110, 130. As such, as the actuators 150, 170 are moved anteriorly or posteriorly, the pivot members 190, 200 slide along the ramps 116, 118, 136, 138 causing the end plates 110, 130 to move toward or away from one another. The pivoting nature of the pivot members 190, 200 allows the angle between the plates 110, 130 to be changed while maintaining the sliding relationship.

Figure 8:
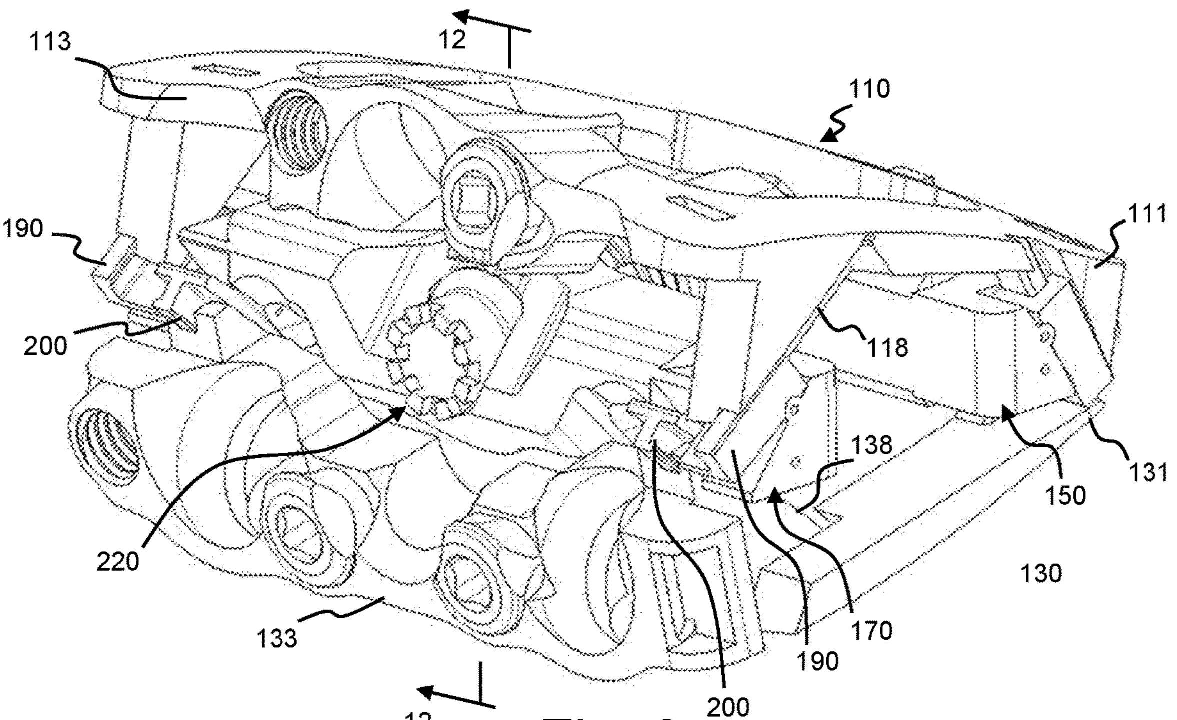
FIG. 8 is a perspective view of the implant of FIG. 1 in an expanded anterior or increased lordotic angle configuration.
Figure 9:
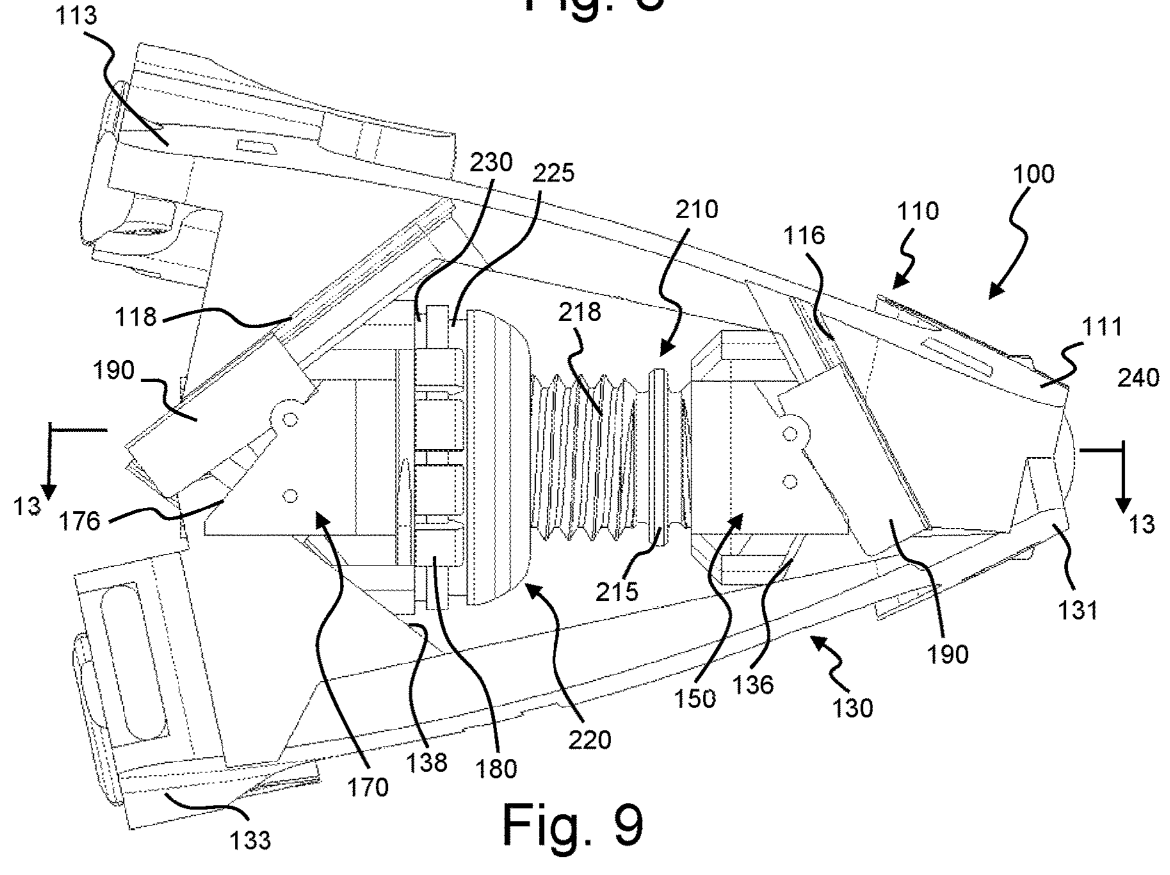
FIG. 9 is a side elevation view of the implant as shown in FIG. 8.
Figure 10:
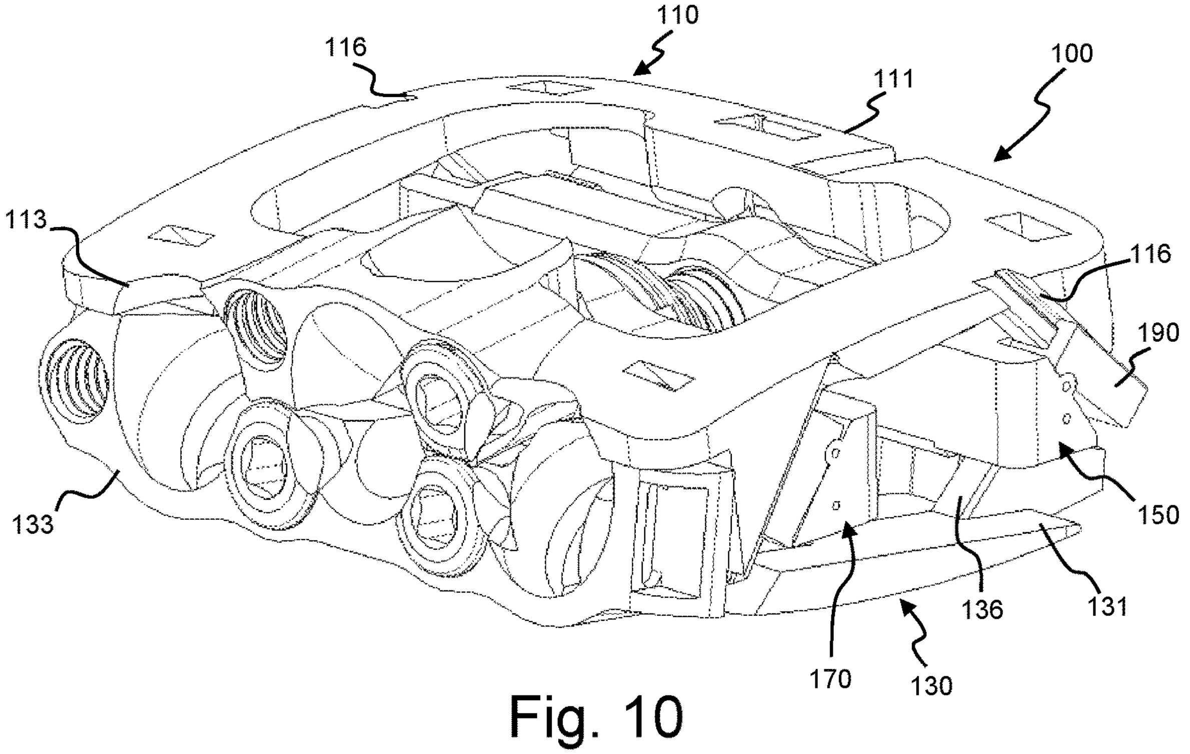
FIG. 10 is a perspective view of the implant of FIG. 1 in an expanded superior or decreased lordotic angle configuration.
Figure 11:
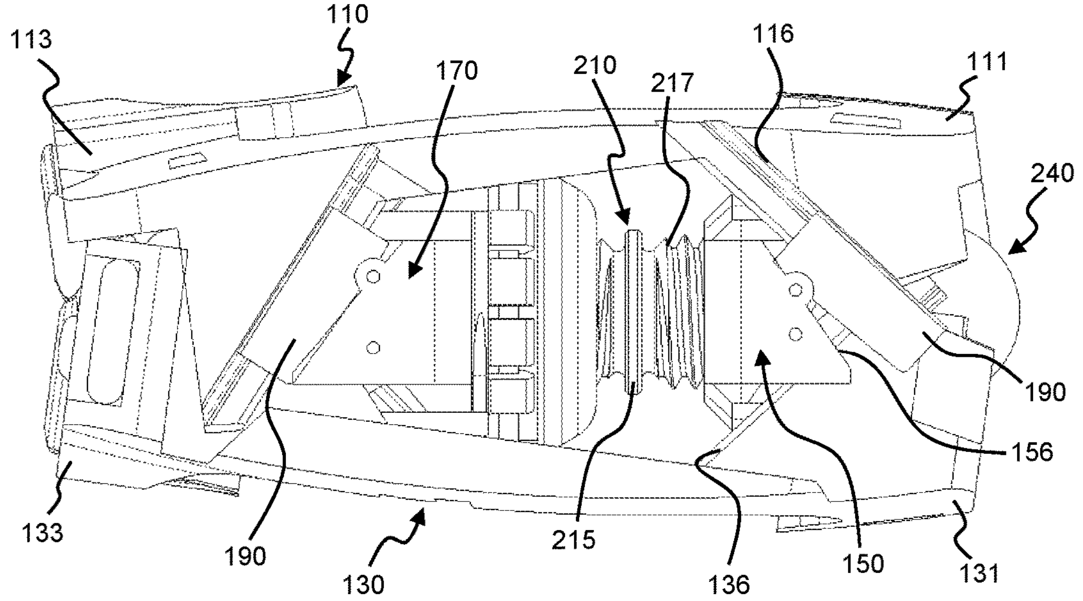
FIG. 11 is a side elevation view of the implant as shown in FIG. 10.

Movement of the actuators 150, 170 and the corresponding movement of the end plates 110, 130 will now be described. FIGS. 2 and 3 illustrate the end plates 110, 130 in the collapsed state and the actuators 150, 170 are both generally centrally located. To move the end plates 110, 130 to the expanded state, the anterior actuator 150 moves anteriorly and the posterior actuator 170 moves posteriorly, as shown in FIGS. 4 and 5. As the actuators 150, 170 move, the pivot members 190, 200 slide along the respective ramps 116, 118, 136, 138. In such expanding actuation, the actuators 150, 170 are moved at the same rate and therefore the end plates 110, 130 maintain the given angle between them and the pivot members 190, 200 generally do not pivot. If it is desired to increase the lordotic angle between the plates 110, 130, the anterior actuator 170 is moved anteriorly while the posterior actuator 150 remains stationary, as illustrated in FIGS. 8 and 9. As the anterior actuator 170 moves, the pivot members 190, 200 slide along the respective ramps 118, 138. Additionally, because the angle between the end plates 110, 130 changes, each of the pivot members 190, 200 pivots relative to its respective actuator 150, 170. Conversely, if it is desired to decrease the lordotic angle between the plates 110, 130, the posterior actuator 150 is moved posteriorly while the anterior actuator 170 remains stationary, as illustrated in FIGS. 10 and 11. As the posterior actuator 150 moves, the pivot members 190 slide along the respective ramps 116, 136. Again, because the angle between the end plates 110, 130 changes, each of the pivot members 190, 200 pivots relative to its respective actuator 150, 170.

Figure 12:
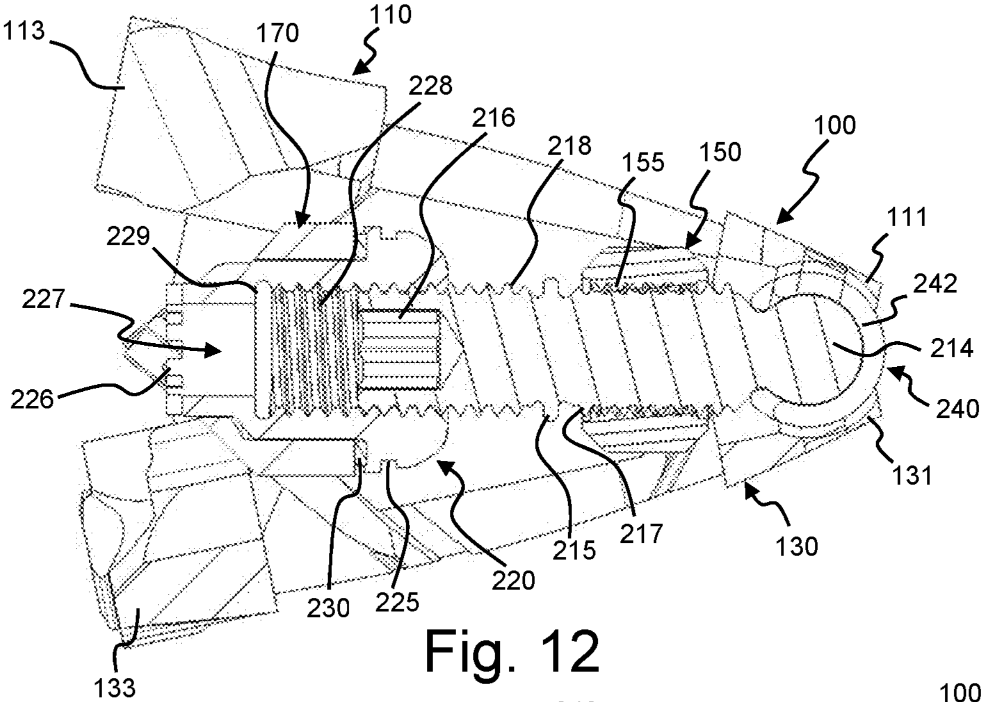
FIG. 12 is a cross-sectional view along the line 12-12 in FIG. 8.
Figure 13:
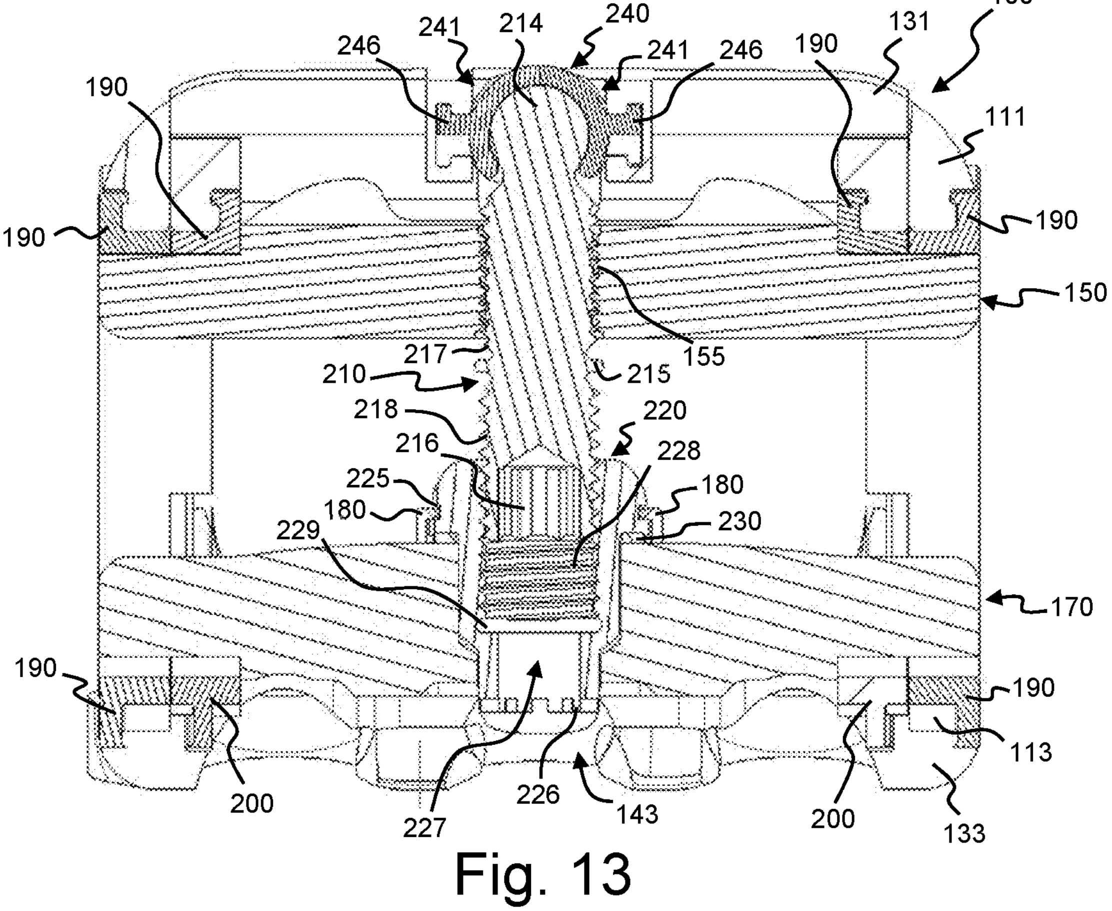
FIG. 13 is a cross-sectional view along the line 13-13 in FIG. 9.

To facilitate movement of the actuators 150, 170, an actuator assembly extends between the actuators 150, 170. Referring to FIGS. 1, 12 and 13, in the present embodiment, the actuator assembly includes an actuator screw 210, an actuator nut 220, and a spherical bearing 240. The actuator screw 210 includes a shaft extending between a posterior end 211 and an anterior end 213. The posterior end 211 of the screw 210 has a ball 214 while the anterior end 213 includes a driver receiver 216. The actuator screw 210 has a first set of threads 217 on the anterior end and a second set of threads 218 on the posterior end with a flange 215 in between. The first and second sets of threads 217, 218 are oppositely handed, i.e. one set is right handed while the other set is left handed. The posterior end 211 of the actuator screw 210 extends through the central through passage 154 of the posterior actuator 150 with the with threads 217 engaged with the internal threads 155.

The ball 214 of the actuator screw 210 extends beyond the posterior actuator 150 and is retained in the spherical bearing 240. In the present embodiment, the spherical bearing 240 is defined by opposed bearing members 241. With reference to FIG. 1, each bearing member 241 has a generally hemispherical bearing surface 242. An arm 244 extends between the bearing surface 242 and a mounting flange 246. Each mounting flange 246 is configured to be received in a respective receiving slot 126, 146 of the upper end plate 110 or the lower end plate 130. With the ball 214 retained between the bearing surfaces 242 and the flanges 246 engaged with the respective end plates 110, 130, the actuator screw 210 is axially fixed relative to the end plates 110, 130 but is free to pivot relative thereto. As such, as the posterior actuator 150 moves along the thread set 217 of the actuator screw 210, the posterior actuator 150 moves relative to the end plates 110, 130.

The actuator nut 220 has a body 222 extending between a posterior end 221 and an anterior end 223. A through passage 227 extends through the body 222 from the anterior end 223 to the posterior end 221. A portion of through passage 227 defines internal threads 228 which are configured to threadably engage the second thread set 218 of the actuator screw 210. A shoulder 229 is defined within the through passage 227 to define a stop for the actuator screw 210. The anterior end 223 of the actuator nut 220 defines a driver engagement 226 about the through passage 227, which in the illustrated embodiment is a series of notches and teeth.

The anterior end 223 of the body 222 of the actuator nut 220 is configured to be received into the non-threaded through passage 174 of the anterior actuator 170. A radial flange 224 extending from the body 222 limits the extent the actuator nut 220 moves into the non-threaded through passage 174. A thrust washer 230 may be positioned between the flange 224 and the anterior actuator 170. A groove 225 is defined in the actuator nut body 222 posteriorly of the flange 224. The fingers 180 extending from the anterior actuator 170 are configured to engage the groove 225 such that the actuator nut 220 is connected to the anterior actuator 170.

The actuator assembly provides three modes of operation. In the first mode of operation, the actuator screw 210 is turned via the driver receiver 216 while the actuator nut 220 is not turned. Engagement of the internal threads 155 of posterior actuator 150 with the first set of threads 217 of the turning actuator screw 210 causes the posterior actuator 150 to move, for example posteriorly. At the same time, since the opposite handed threads 218 of the turning actuator screw 210 are engaging the internal threads 218 of the non-turning actuator nut 220, the actuator nut 220, and thereby the anterior actuator 170, are caused to move in the opposite direction, in this example, anteriorly. This results in both actuators 150, 170 moving toward the ends of the end plates 110, 130 and gives linear expansion with both endplates 110, 130 expanding the same distance (FIGS. 4 and 5). Turning the actuator screw 210 in the opposite direction would move the end plates 110, 130 toward one another.

In the second mode of operation, the actuator screw 210 is not turned while the actuator nut 220 is turned via the driver engagement 226. Since the actuator screw 210 is not turning, the posterior actuator 150 does not move. However, as the actuator nut 220 turns relative to the thread set 218 of the stationary actuator screw 210, the actuator nut 220, and thereby the anterior actuator 170, move alone which expands the anterior end of each endplate only and results in an increase in lordotic angle. (FIGS. 8 and 9). Turning the actuator nut 220 in the opposite direction would move the anterior ends of end plates 110, 130 toward one another.

In the third mode of operation, the actuator screw 210 is turned via the driver receiver 216 while the actuator nut 220 is also turned via the driver engagement 226. Since the actuator screw 210 and the actuator nut 220 are turning at the same rate, there is no relative movement between the actuator nut 220 and the actuator screw 210. As such, the anterior actuator 170 does not move. However, the turning actuator screw 210 causes the posterior actuator 150 to move alone which expands the posterior end of each endplate only and results in a reduction in lordosis. (FIGS. 10 and 11). Turning the actuator screw and actuator nut 220 simultaneously in the opposite direction would move the posterior ends of end plates 110, 130 toward one another.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients may be advantageously treated, for example, who may have spondylolisthesis up to grade 1 at the involved level. The surgery position implant 100 may be performed through an anterior, anterolateral, posterolateral, and/or lateral approach. Various implant methods are disclosed in US 2014/0277489, the contents of which are incorporated herein by reference in its entirety for all purposes. During implantation, the driver receiver 216 and driver engagement 226 may be engaged by separate tools or an integrated tool to actuate the actuator assembly.

Referring to FIGS. 17-21, an implant 300 in accordance with another embodiment of the disclosure will be described. The implant 300 includes features that are substantially similar to that of the implant 100 described above. As such, a description of these features will be omitted in the description of the implant 300 for clarity. Similar to the implant 100, the implant 300 also includes upper and lower endplates 110, 130, anterior and posterior actuators 350, 370, an actuator screw 210, an actuator nut 220, a spherical bearing 240 and a thrust washer 230. In some embodiments, the implant may include a plurality of blocking screws 124 on the endplates 110, 130 to prevent migration of the fixation screws or anchors. Each of the actuators 350, 370 includes a pair of cylindrical protrusions 302 extending from opposite ends of each actuator. Instead of the sliding pivot members of the implant 100 described above, the implant 300 includes rotational pivot assemblies 390. Each of the plurality of rotational pivot member assemblies 390 includes a first pivot member 392 and a second pivot member 394, both of which are slidably coupled to the cylindrical protrusions 302 of the actuators 150, 170 to facilitate expansion and contraction of the plates 110, 130.

Figure 18:
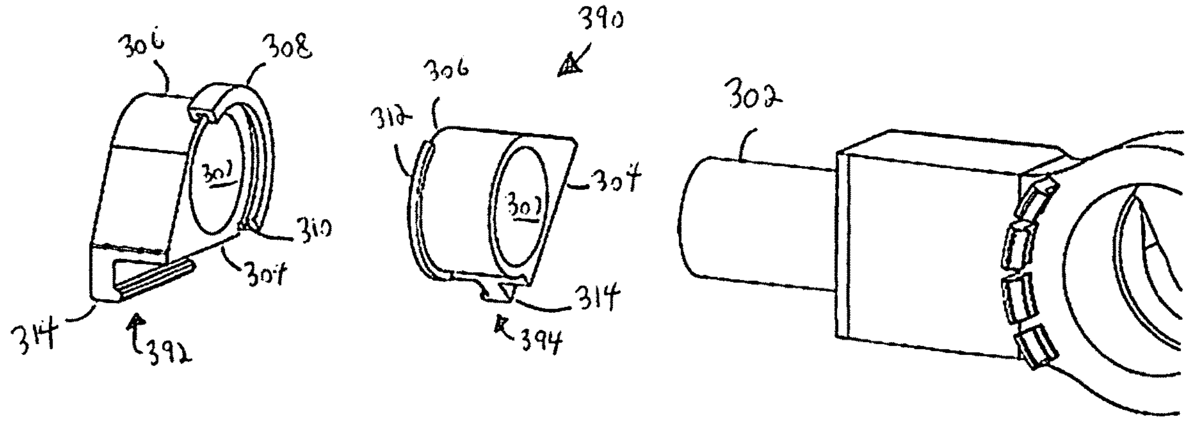
FIG. 18 is a close up view of a pivot member assembly in accordance with an embodiment of the disclosure.

As shown more clearly in FIG. 18, both the first and second pivot members 392, 394 include a flat portion 304 and a cylindrical portion 306. The cylindrical portion 306 includes an opening 307 configured to receive the cylindrical protrusion 302 of the actuators. The first pivot member 392 includes a first lip 308 extending from the cylindrical portion 306 of the first pivot member 392. The first lip 308 includes a groove 310 configured to receive a second lip 312 extending from the cylindrical portion 306 of the second pivot member 394 to facilitate coupling of the second pivot member 392 to the first pivot member 390 such that their respective openings are aligned. In some embodiments, the first and second pivot members 392, 394 are coupled to one another before coupling the pivot member assembly 390 to the cylindrical protrusion 302 of a respective actuator. Each flat portion 304 includes a protrusion 314 extending from the flat portion 304 and configured to be inserted into grooves (e.g., grooves 117, 119, 137, 139) of the upper and lower endplates 110, 130 to allow the pivot members 392, 394 to slide against the guide ramps (e.g., 116, 118, 136, 138) of the endplates during actuation of actuator screw 210. In some embodiments, the protrusions 314 (and the corresponding grooves) may have an L-shaped cross-section to improve the stability and rigidity of the coupling of the pivot members 392, 394 to the guide ramps. The pivot members 392, 394 are pivotally connected to respective ones of the actuators 350, 370 and slide along the respective guide ramps as the plates 110, 130 expand or contract.

The rotational pivot member assemblies 390 are each pivotally connected to and thereby rotate relative to the respective cylindrical protrusion 302 of the corresponding actuator 350, 370 while also being engaged with the grooves 117, 119, 137, 139 in the upper and lower end plates 110, 130. As such, as the actuators 350, 370 are moved anteriorly or posteriorly, the rotational pivot member assemblies 390 rotate with respect to their respective cylindrical protrusions and slide along the ramps 116, 118, 136, 138 causing the end plates 110, 130 to move toward or away from one another. The pivoting nature of the rotational pivot member assemblies 390 allows the angle between the plates 110, 130 to be changed while maintaining the sliding relationship.

Figure 19:
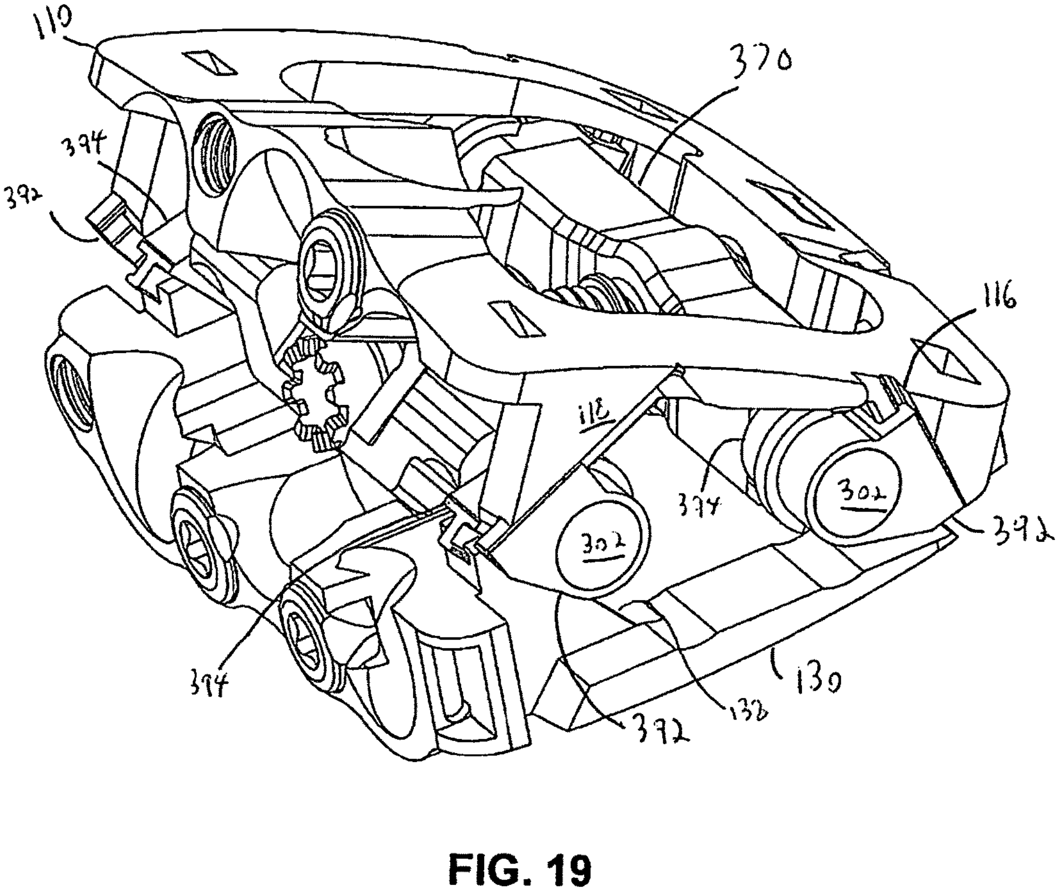
FIG. 19 is a perspective view of the implant of FIG. 17 in an expanded anterior or increased lordotic angle configuration.
Figure 20:
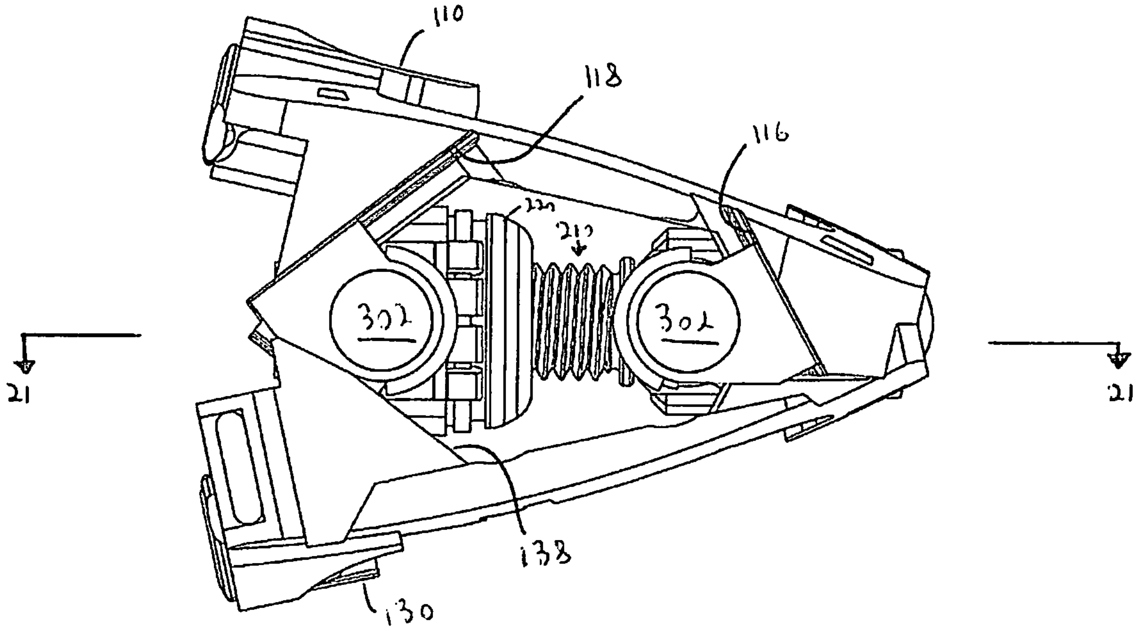
FIG. 20 is a side elevation view of the implant as shown in FIG. 19.
Figure 21:
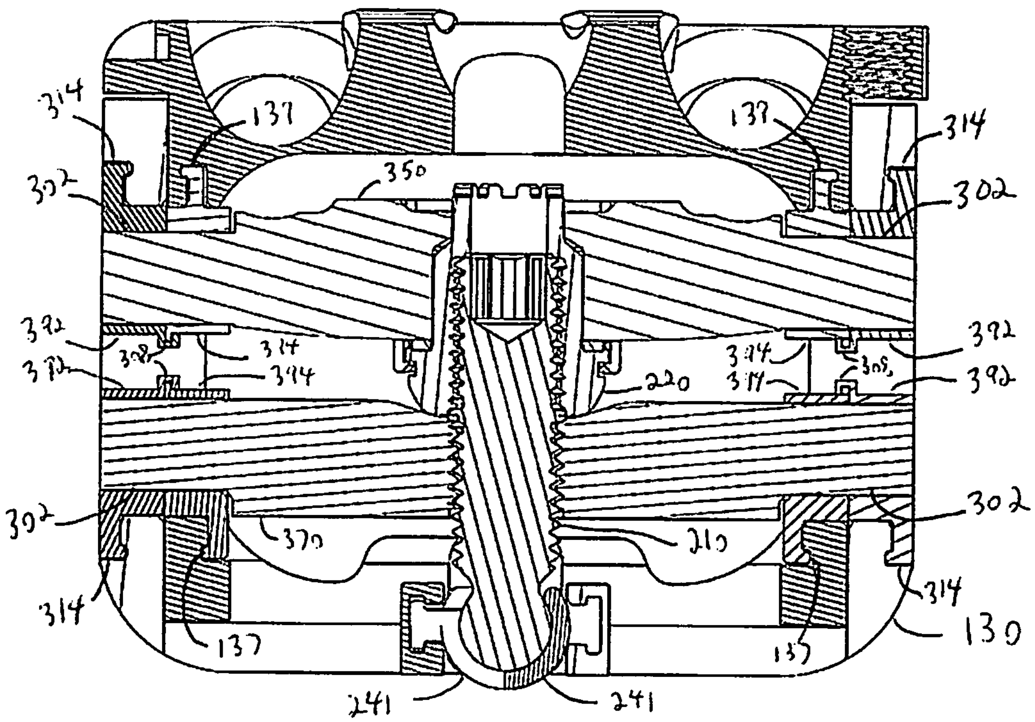
FIG. 21 is a cross-sectional view along the line 21-21 in FIG. 20.
Figure 22:
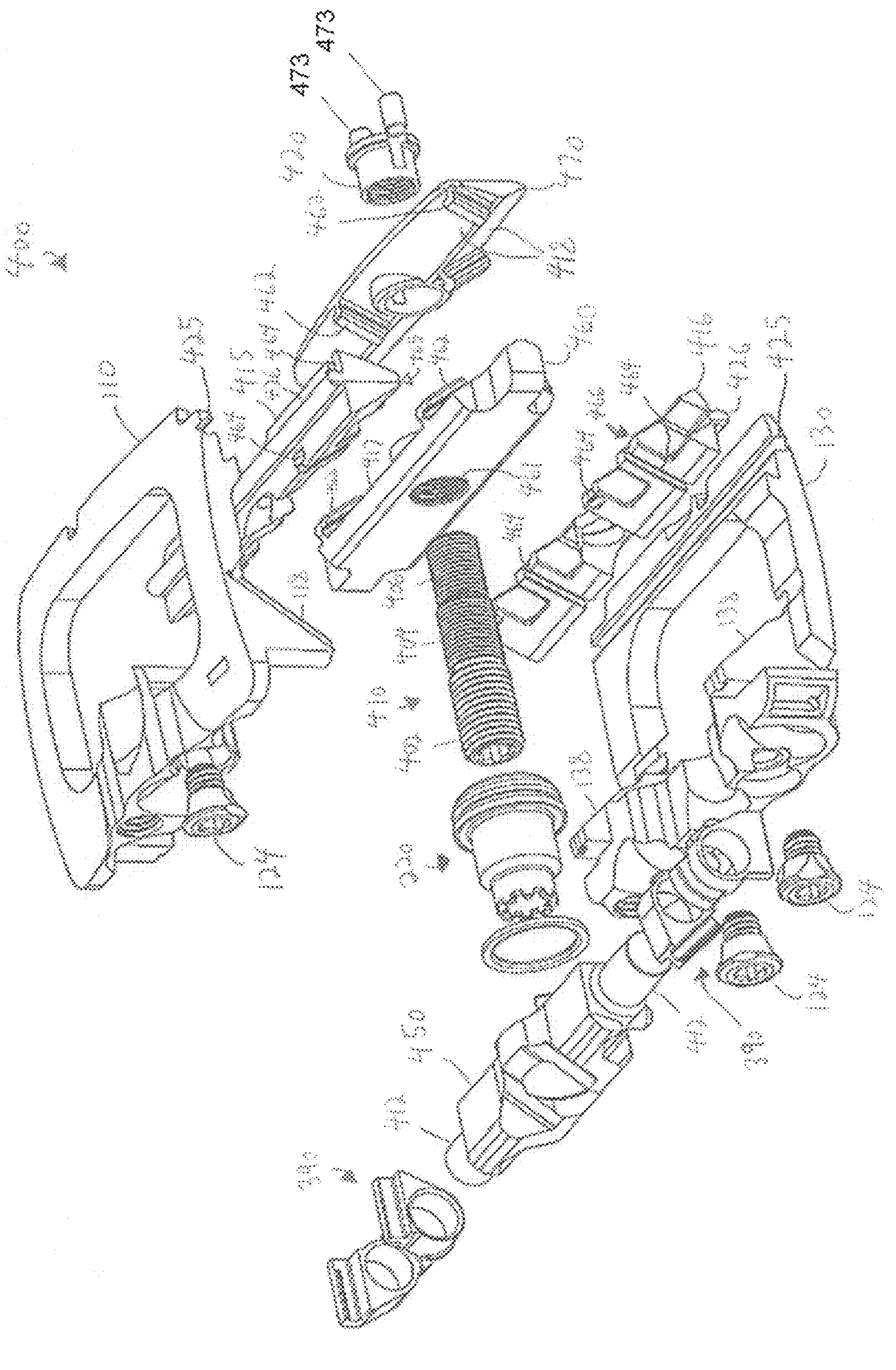
FIG. 22 is an exploded perspective view of an implant in accordance with an embodiment of the disclosure.

Movement of the actuators 350, 370 and the corresponding movement of the end plates 110, 130 is similar to the movement of the actuators 350, 370 described above. For example, in the one mode of operation (similar to the second mode of operation described above), the actuator screw 210 is not turned while the actuator nut 220 is turned via the driver engagement 226. Since the actuator screw 210 is not turning, the posterior actuator 350 does not move. However, as the actuator nut 220 turns relative to the thread set 218 of the stationary actuator screw 210, the actuator nut 220, and thereby the anterior actuator 170, move alone which expands the anterior end of each endplate only and results in an increase in lordotic angle. (FIGS. 19 and 20).

Referring to FIGS. 22-26, an implant 400 in accordance with another embodiment of the disclosure will be described. The implant 400 includes features that are substantially similar to that of the implant 300 described above. As such, a description of these features will be omitted in the description of the implant 400 for clarity. Similar to the implant 300, the implant 400 also includes upper and lower endplates 110, 130, an actuator screw 410, and an actuator nut 220. In some embodiments, the implant 400 may also include a plurality of blocking screws 124 on the endplates 110, 130 to prevent migration of the fixation screws or anchors. The implant 400 differs from the implant 300, however, in that the implant 400 includes an anterior actuator 450, a second actuator 460, a posterior actuator 470, a first endplate pivot 415, a second endplate pivot 416, and a second actuator nut 420.

In some embodiments, the actuator screw 410 includes right hand threads in a first portion 402 and a third portion 406 and left hand threads in a second portion 404 disposed between the first and third portions 402, 406. It should be noted, however, that in some embodiments, the first and third portions 402, 406 may instead have left-handed threads and the second portion 404 has right-handed threads. The anterior actuator 450 is threaded onto the first portion 402 of the actuator screw 410 via the actuator nut 220. The second actuator 460 includes a through hole 461 having threads that are threaded onto the second portion 404 of the actuator screw 410. The posterior actuator 470 includes a through hole 471 into which the third portion 406 of the actuator screw 410 passes. The second actuator nut 420 includes a through hole 421 having threads that are threaded onto the threads of the third portion 406 of the actuator screw 410. In some embodiments, the second actuator nut 420 is press-fitted into the posterior actuator 470. In some embodiments, the second actuator nut 420 is alternatively threaded into the posterior actuator 470. In such an embodiment, the second actuator nut 420 includes external threads that correspond to internal threads on the opening formed through the posterior actuator 470. In either of these embodiments, one or more pins 473 are inserted into corresponding channels 475 which are formed partially in the posterior actuator 470 and partially in the second actuator nut 420. The one or more pins 473 are configured to prevent rotation of the second actuator nut 420 when the actuator screw 410 rotates within the second actuator nut 420.

Figure 23:
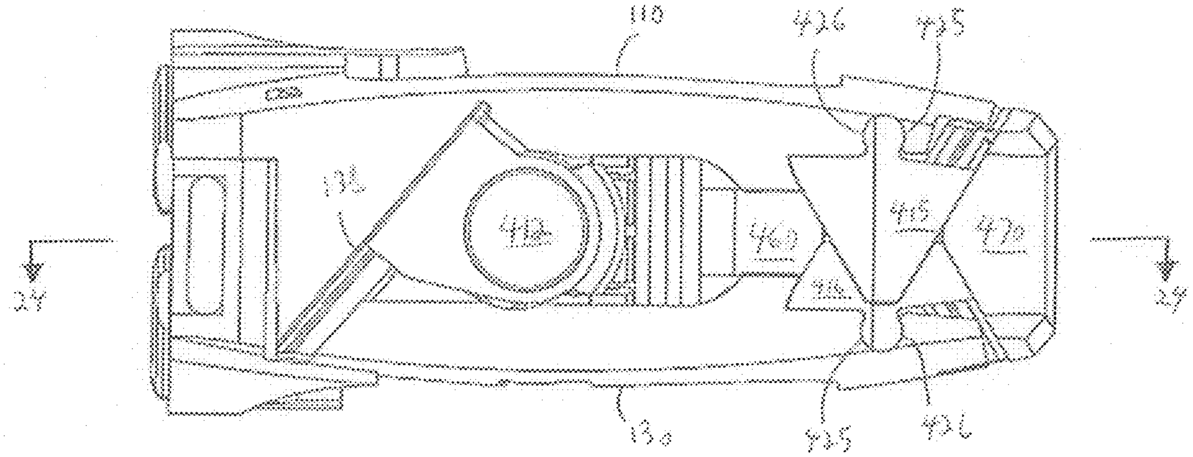
FIG. 23 is a side view of the implant of FIG. 22 in a compressed configuration.
Figure 24:
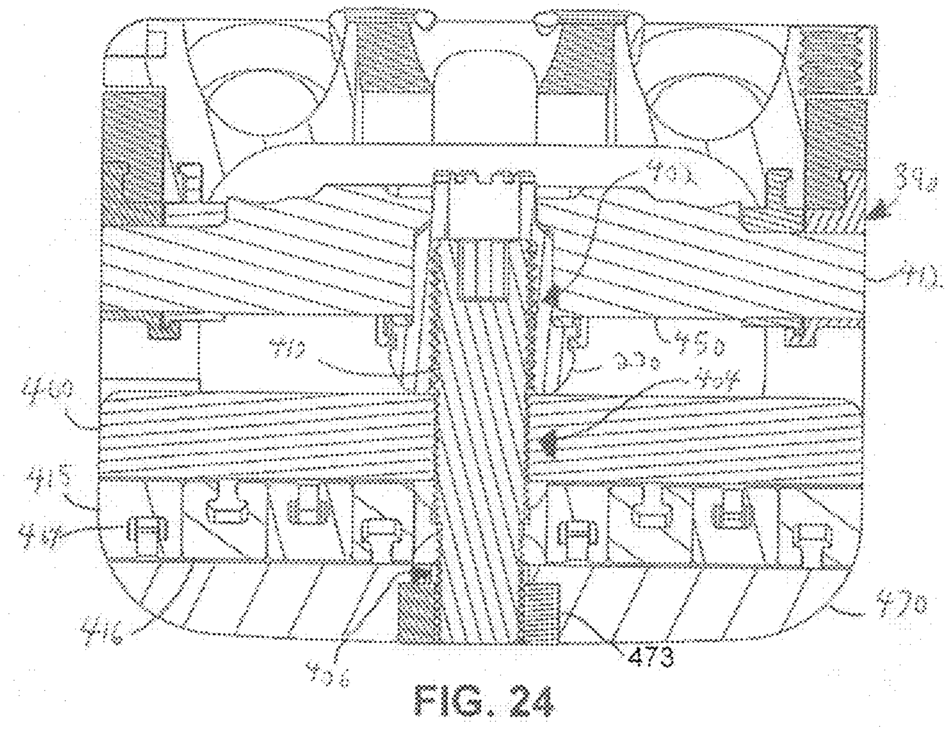
FIG. 24 is a cross-sectional view along the line 24-24 in FIG. 23
Figure 25:
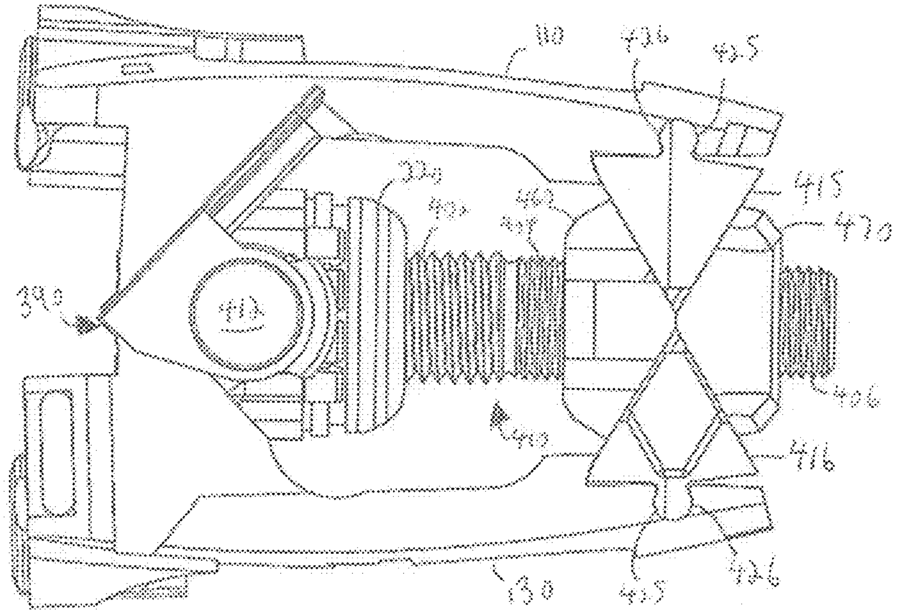
FIG. 25 is a side view of the implant of FIG. 22 in an expanded anterior and posterior configuration.
Figure 26:
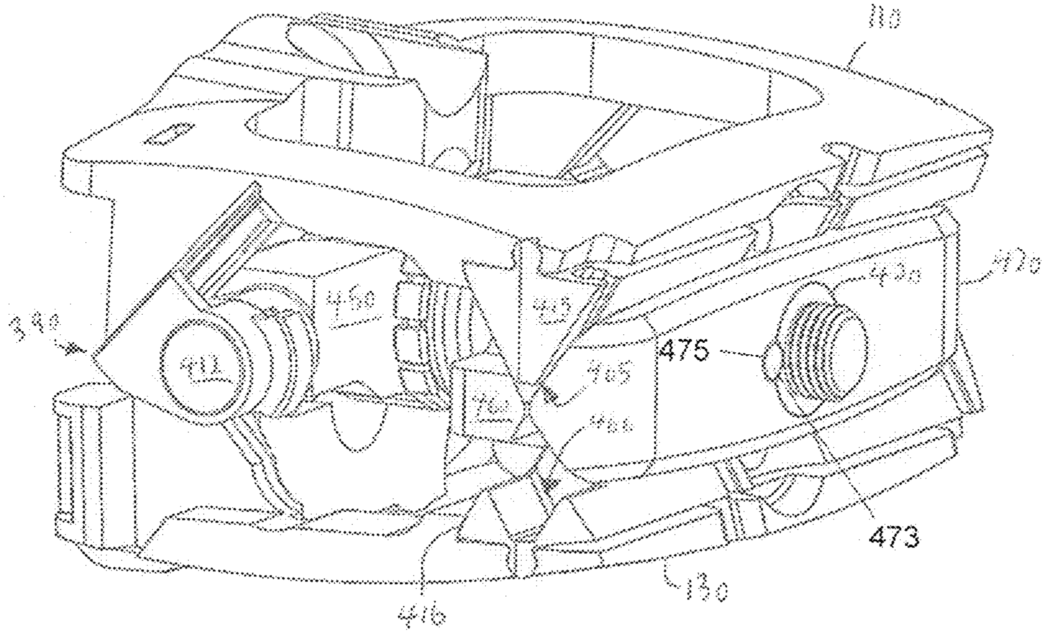
FIG. 26 is a perspective view of the implant of FIG. 22 in an expanded anterior and posterior configuration.
Figure 27A:
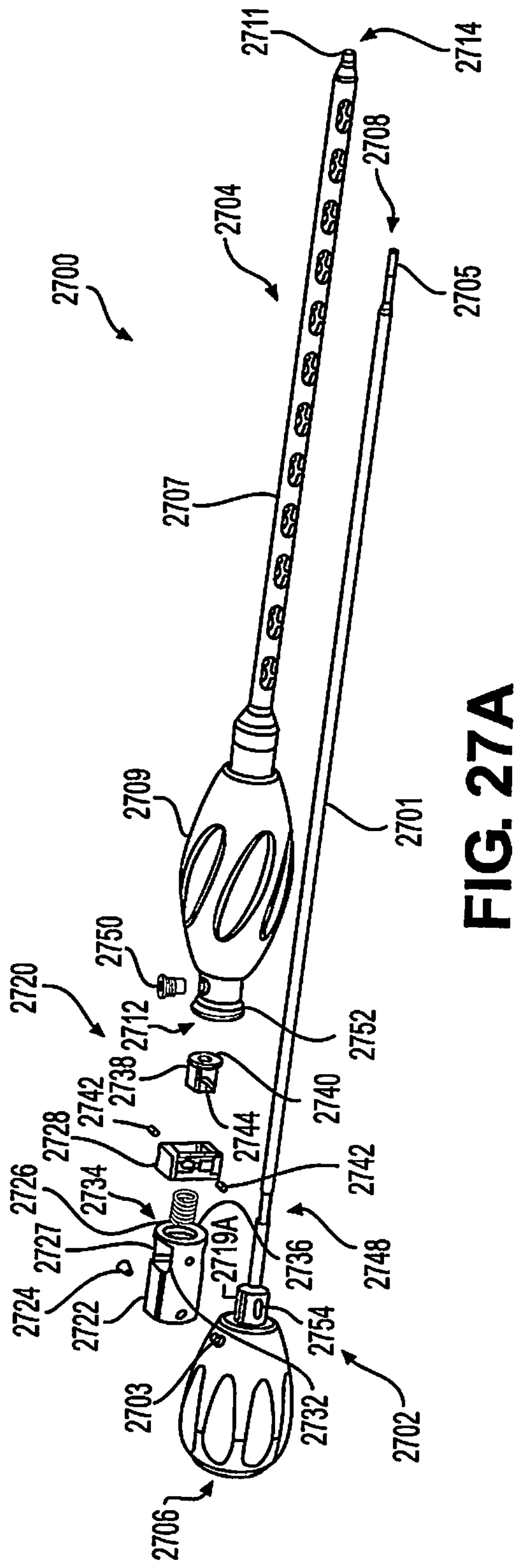
FIGS. 27A-27C are exploded views of a bi-directional driver according to embodiments of the present disclosure for use with an expandable implant.
Figure 27B:
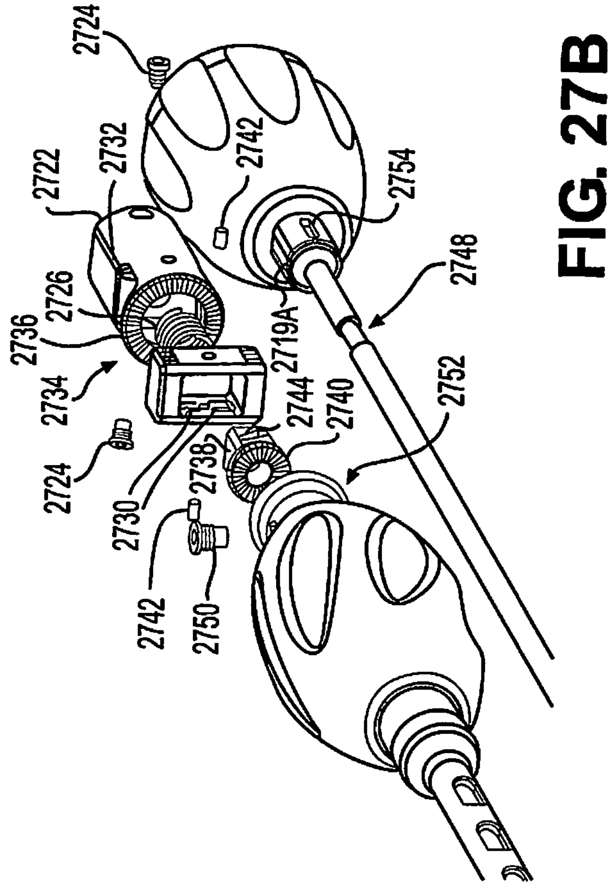
Figure 27C:
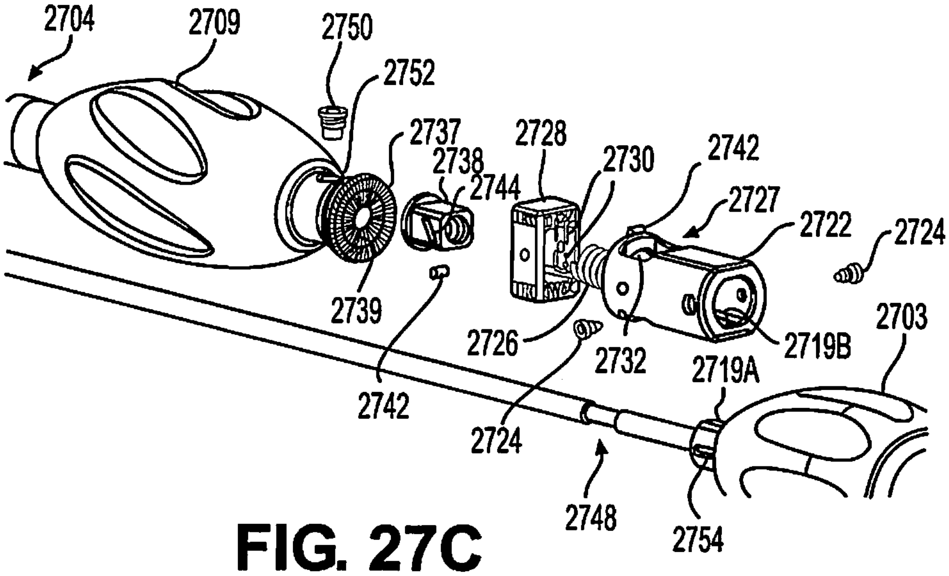

In some embodiments, the anterior actuator 450 includes cylindrical protrusions 412 (similar to the cylindrical protrusions 302) onto which rotational pivot member assemblies 390 are slidably coupled. Each of the pivot member assemblies 390 is coupled to grooves formed in the ramps 118, 138 at a first end 313 of the endplates 110, 130, as described above with respect to the implant 300. The first and second endplate pivots 415, 416 slide on the ramp surfaces 417, 418 of the second and posterior actuators 460, 470, respectively. Each endplate pivot includes grooves 464 formed on the anterior and posterior sides of the endplate pivot and configured to receive corresponding protrusions 462 extending from the second and posterior actuators 460, 470. In some embodiments, the grooves 464 and the protrusions 462 have a T-shaped cross-section to improve the stability of the slidable coupling of the endplate pivots to the actuators. As shown more clearly in FIG. 22, a downward-facing portion 465 of the first endplate pivot and an upward-facing portion 466 of the second endplate pivot 416 are shaped such that the upward and downward-facing portions 465, 466 mate when the implant 400 is in a contracted position, as shown in FIGS. 23 and 24. In some embodiments, each endplate includes a groove 425 configured to receive a protrusion 426 extending from one of endplate pivots 415, 416.

The implant 400 has three modes of operation. In the first mode of operation, the actuator screw 410 is turned and the actuator 220 nut is not turned. As a result, the anterior actuator 450 moves away from the second actuator 460, the second actuator 460 moves away from the anterior actuator 450, and the posterior actuator 470 moves towards the second actuator. This results in the anterior actuator 450 separating the ends of both endplates adjacent the anterior actuator 450 while the second and posterior actuators 460, 470 combine to separate the opposite ends of the implant 400. The resulting expansion is linear, where the anterior and posterior ends of the implant separate at the same rate. Turning the actuator screw 410 clockwise will expand the implant 400 whereas turning the actuator screw 410 counter-clockwise will contract the implant.

In the second mode of operation, the actuator screw 410 is not turned and the actuator nut 220 is turned. As a result, the anterior actuator 450 moves alone, which expands only the end of implant adjacent the anterior actuator 450, causing an increase in lordotic angle. Turning the actuator nut 220 counter-clockwise will increase this lordosis.

In the third mode of operation, the actuator screw 410 and the actuator nut 220 are turned together, which moves only the second and posterior actuators 460, 470, resulting in expansion of the ends of the implant 400 adjacent the posterior actuator 470. The resulting configuration effects a reduction in lordosis. When the actuator screw 410 and actuator nut 220 are both turned clockwise, a reduction in lordosis/posterior expansion is effected.

Referring to FIGS. 27A-28H, a bi-directional driver 2700 in accordance with embodiments of the present disclosure will be described. The bi-directional driver 2700 may be used, for example, to expand or collapse an implant (e.g., the implants described above). In some embodiments, the bi-directional driver 2700 includes an inner driver 2702 configured to be disposed within an outer driver 2704. The inner driver 2702 includes a shaft 2701 extending from a handle 2703 at a proximal end 2706 to an inner driver tip 2705 at a distal end 2708. Similarly, the outer driver 2704 includes a tubular shaft 2707 extending from a handle portion 2709 at a proximal end 2712 to an outer driver tip 2711 at a distal end 2714.

In some embodiments, the bi-directional driver 2700 includes a rotational constraint system 2720 that that couples the inner and outer drivers 2702, 2704 such that the inner driver 2702 is allowed to turn clockwise or counter-clockwise while the outer driver 2704 is allowed to either turn in the same direction as the inner driver 2702 or prevented from turning. In some embodiments, the rotational constraint system 2720 includes a locking sleeve 2722 coupled to the shaft 2701 of the inner driver 2702 via a fixation element 2724 (e.g., a screw) proximate the handle 2703. In some embodiments, an interior of the locking sleeve 2722 and the portion of the shaft 2701 that extends through the locking sleeve 2722 may include mating flat surfaces 2719A, 2719B to prevent the relative rotation of the locking sleeve 2722 with respect to the shaft 2701. A distal end 2734 of the locking sleeve 2722 includes a plurality of ratcheting teeth 2736 configured to mesh with and engage a first set of ratcheting teeth 2737 on a proximal end of the outer driver 2704 (discussed below).

The locking sleeve 2722 includes an opening 2727 configured to house a push button 2728, which is used by a user to choose the direction (clockwise or counterclockwise) desired to turn the inner driver 2702. In some embodiments, the push button 2728 may include one or more leaf spring elements 2730 configured to interface with edges 2732 of the opening 2727 so that the push button 2828 is captured at either side of its stroke.

A ratchet pusher 2738 is disposed within the push button 2728. The ratchet pusher 2738 includes a plurality of ratcheting teeth 2740 at is distal end which are configured to mesh with and engage a second set of ratcheting teeth 2739, which are disposed at the proximal end of the outer driver 2704 and concentric to the first set of ratcheting teeth 2737. The ratcheting teeth 2740 of the ratchet pusher 2738 are oriented in a direction opposite a direction of the ratcheting teeth 2736 of the locking sleeve 2722 and are concentric to the ratcheting teeth 2736. Similarly, the second set of ratcheting teeth 2739 are oriented in a direction opposite a direction of the first set of ratcheting teeth 2737. As a result, when the ratcheting teeth 2736 of the locking sleeve 2722 engage the first set of ratcheting teeth 2737, relative rotation between the inner and outer drivers 2702, 2704 is allowed in a first direction. For example, the inner driver 2702 is allowed to rotate in a clockwise direction while the outer driver 2704 can be held still or rotated counterclockwise. However, both the inner and outer drivers 2702, 2704 can be rotated counterclockwise together (i.e., not independent of one another). Alternatively, when the ratcheting teeth 2740 of the ratchet pusher 2738 engage the second set of ratcheting teeth 2739, relative rotation between the inner and outer drivers 2702, 2704 is allowed in a second direction. For example, the inner driver 2702 is allowed to rotate in a counterclockwise direction while the outer driver 2704 can be held still or rotated clockwise. However, both the inner and outer drivers 2702, 2704 can be rotated clockwise together (i.e., not independent of one another).

To facilitate movement of the ratcheting teeth 2740 of the ratchet pusher 2738 into and out of engagement with the second set of ratcheting teeth 2739, a pair of pins 2742 extend from opposite sides of the push button 2728 and into a corresponding pair of angled slots 2744 formed in the ratchet pusher 2738. The slots 2744 are angled such that when the push button 2728 is in a first position, the ratcheting teeth 2736 of the locking sleeve 2722 engage the first set of teeth, as depicted in FIGS. 28A-28D, and when the push button 2728 is in a second position, the ratcheting teeth 2740 of the ratchet pusher 2738 engage the second set of ratcheting teeth 2739, as depicted in FIGS. 28E-28H. Vertical movement of the push button 2728 between the first and second positions imparts either a distal or proximal force on the ratchet pusher 2738 due to the constraint of the pair of pins 2742 within the angled slots 2744. This results in the ratchet pusher 2738 being pushed into and out of engagement with the second set of ratcheting teeth 2739.

In use, the inner driver tip 2705 may be configured to engage the actuator screw 410 and the outer driver tip 2711 may be configured to engage the actuator nut 220 to effectuate the first, second, and third modes of operation discussed above. In some embodiments, the locking sleeve 2722 is coupled to the inner driver 2702 via the one or more screws 2724 to prevent any relative rotational movement between the locking sleeve 2722 and the inner driver 2702. In some embodiments, the screws 2724 are threaded into the screws 2746 are threaded into corresponding slots 2754 to allow for translation of the locking sleeve 2722 along the inner driver 2702 to allow for linear translation of the locking sleeve 2722 along the inner driver 2702, which results in in a change in the distance between the distal most tip of the inner driver 2702 and the distal most tip of the outer driver 2704 (since the outer driver translates along the inner driver 2702 with the locking sleeve 2722). This translation is useful since the actuator nut 220 moves along the actuator 410. As such, the distance between the engagement portion of the actuator nut 220 and the engagement portion of the actuator screw 410 changes, which is compensated for by the change in distance between the distal most tip of the inner driver 2702 and the distal most tip of the outer driver 2704.

Figure 28A:
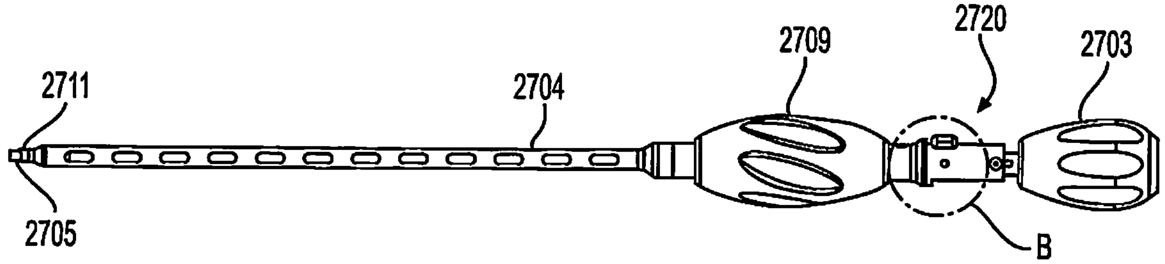
FIGS. 28A-28H depict the bi-directional driver of FIGS. 27A-27C in an assembled state.
Figure 28B:
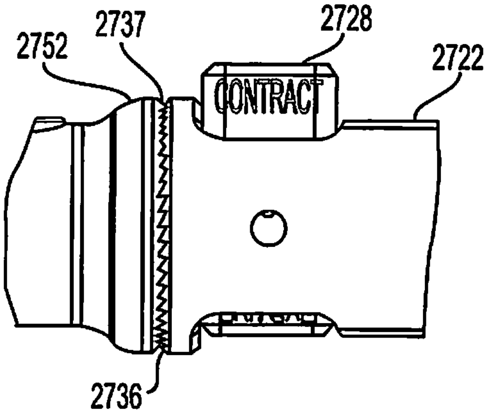
Figure 28C:
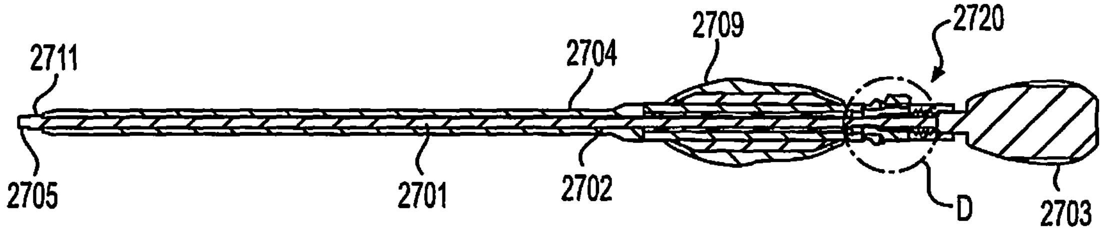
Figure 28D:
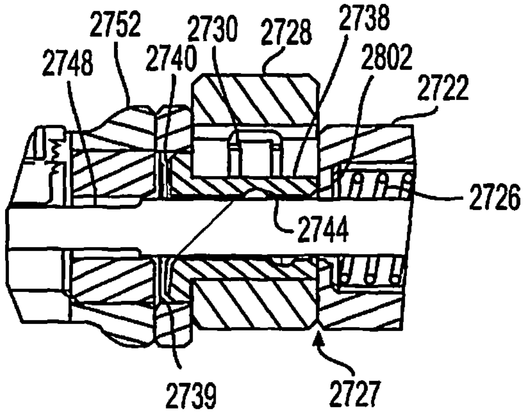
Figure 28E:
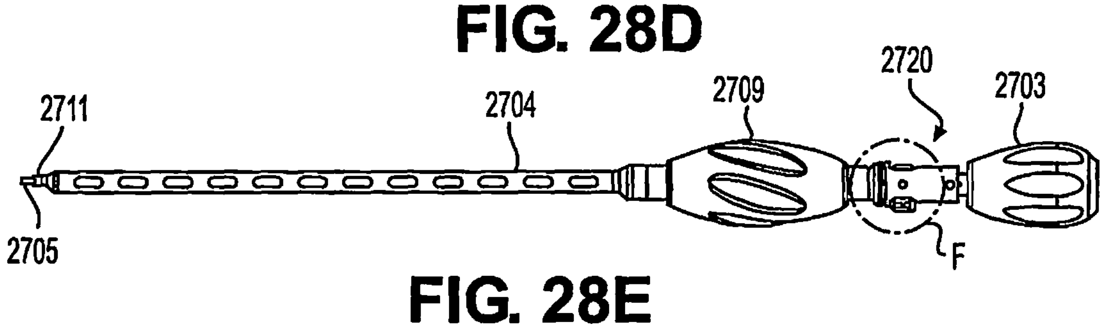
Figure 28F:
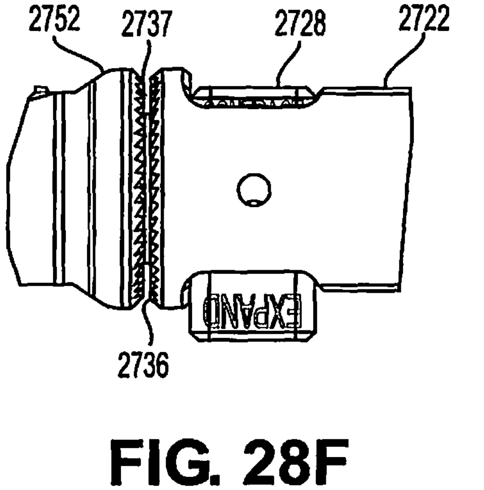
Figure 28G:
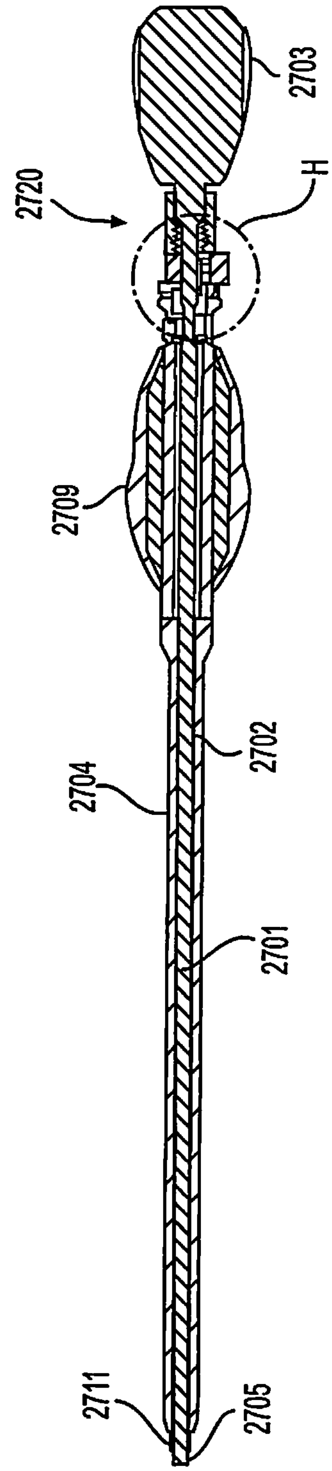
Figure 28H:
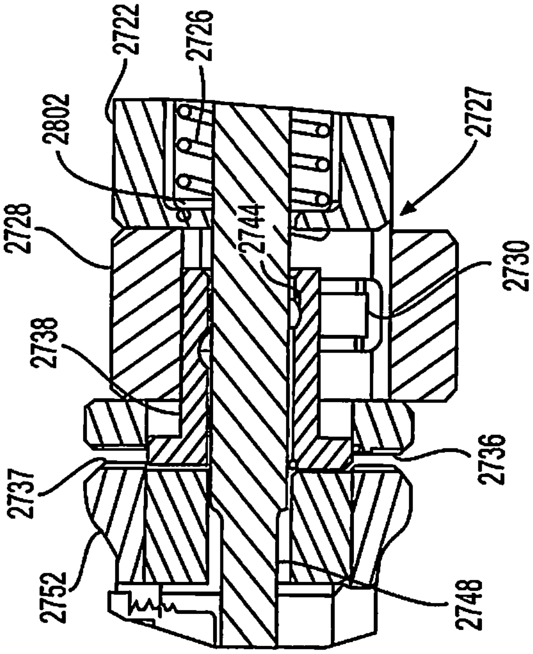
Figure 29A:
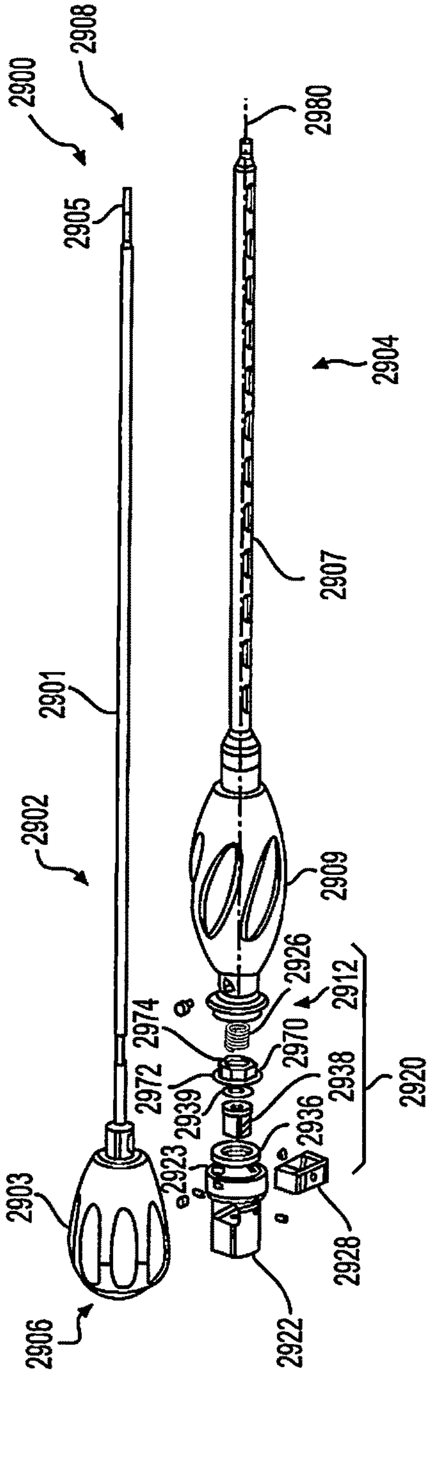
FIGS. 29A-29D are exploded views of a bi-directional driver according to embodiments of the present disclosure for use with an expandable implant.
Figure 29B:
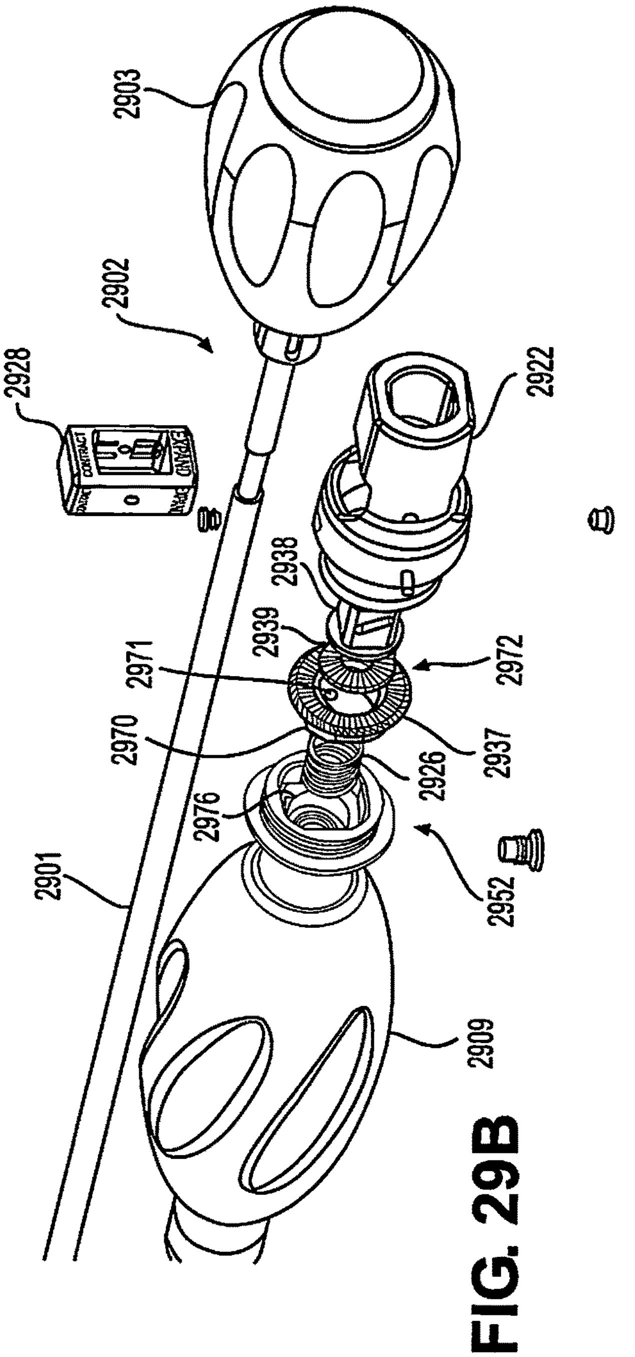
Figure 29C:
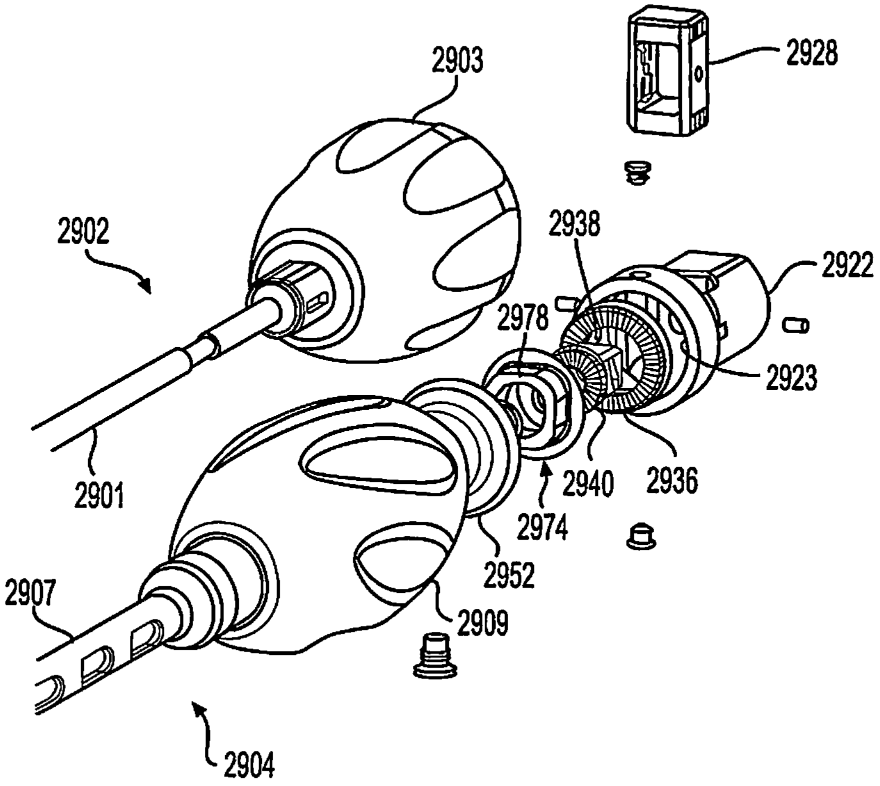
Figure 29D:
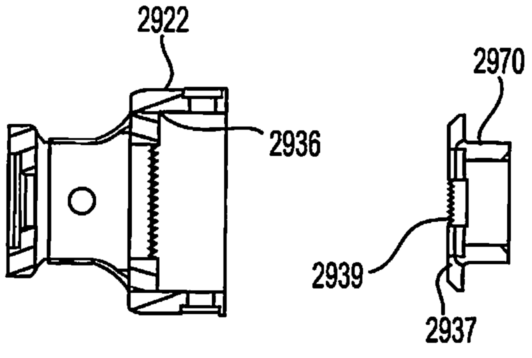

In some embodiments, a biasing element 2726 is disposed within the locking sleeve 2722 and extends between the handle 2703 and a radially inwardly extending wall 2802 (shown more clearly in FIGS. 28D and 28H). The biasing element 2726 is configured to bias the locking sleeve 2722 towards the distal end 2708. In some embodiments, the biasing element 2726 may be a helical spring. However, it should be noted that the biasing element 2726 may alternatively be any type of biasing device that is capable of biasing the locking sleeve 2722 as described above (e.g., a leaf spring). The linear translation of the locking sleeve 2722 along the inner driver and the biasing element 2726 facilitate a spring loaded initial position (i.e., engagement of the ratcheting teeth 2736 of the locking sleeve 2722 with the first set of ratcheting teeth 2737).

The handle portion 2709 of the outer driver 2704 is coupled to the inner driver 2702 via a screw 2750. The screw 2750 extends through a collar 2752 of the handle portion 2709 and into a reduced diameter section 2748 formed in the shaft 2701 of the inner driver, which allows for relative rotation between the handle portion 2709 (and thus, the outer driver 2704) and the inner driver 2702 and limited relative translation between these two elements as well.

Referring now to FIGS. 29A-30H, a bi-directional driver 2900 in accordance with embodiments of the present disclosure will be described. The bi-directional driver 2900 functions similarly to the bi-directional driver 2700 described above and includes similar components. As such, a description and labelling of some of these similar components will be omitted here and in the figures for clarity and brevity.

Similar to the bi-directional driver 2700, the bi-directional driver 2900 includes a rotational constraint system 2920 and an inner driver 2902 configured to be disposed within an outer driver 2904. The inner driver 2902 includes a shaft 2901 extending from a handle 2903 at a proximal end 2906 to an inner driver tip 2905 at a distal end 2908. Similarly, the outer driver 2904 includes a tubular shaft 2907 extending from a handle portion 2909 at a proximal end 2912 to an outer driver tip 2911 at a distal end 2914.

A locking sleeve 2922 of the bi-directional driver 2900 also houses a push button 2928 similar to the push button 2727 including similar functionality. However, in some embodiments, the locking sleeve 2922 may include a distal opening 2923 configured to receive an outer ratchet teeth ring 2936 within. The ratchet pusher 2938 extends through the locking sleeve 2922 and the outer ratcheting teeth ring 2936. Similar to the ratchet pusher 2738, the distal end of the ratchet pusher 2938 includes a plurality of ratchet teeth 2940 concentric with the outer ratchet teeth ring 2936.

The bi-directional driver 2900 further differs from the bi-directional driver 2700 in that the two sets of ratcheting teeth are not formed directly at a proximal end of the handle portion 2909 of the outer driver 2904. Instead, a slider 2970 having a proximal end 2972 and a distal end 2974 includes a first set of ratcheting teeth 2937 at the proximal end 2972. A second set of ratcheting teeth 2939 in the form of a ring is pressed into an opening 2971 formed in the proximal end 2972 of the slider 2970 such that the first and second sets of ratcheting teeth 2937, 2939 are concentric. A collar 2952 of the handle portion 2909 includes an opening 2976 which has a shape corresponding to a shape of an exterior surface 2978 of the slider 2970 such that the slider 2970 is inserted into the opening 2976. The shape of the exterior surface 2978 and the opening 2976 is configured to prevent rotation of the slider 2970 within the opening 2976 but to allow for translation of the slider 2970 along a longitudinal axis 2980 of the outer driver 2904.

In some embodiments, a biasing element 2926 is disposed within the opening 2976 to bias the slider 2970 proximally. In some embodiments, the biasing element 2926 may be, for example, a helical spring. However, it should be noted that other biasing elements are contemplated (e.g., a leaf spring).

The functionality of the bi-directional driver 2900 is similar to that of the bi-directional driver 2700 described above. Specifically, actuation of the push button 2928 moves the ratcheting teeth 2940 of ratchet pusher 2938 into and out of engagement with the second set of ratcheting teeth 2939. As illustrated in FIGS. 30A-30D, the biasing element 2926 biases the slider 2970 proximally such that the first set of ratcheting teeth 2937 is biased against the outer ratcheting teeth ring 2936, which is the initial state of the bi-directional driver 2900.

Figure 30A:
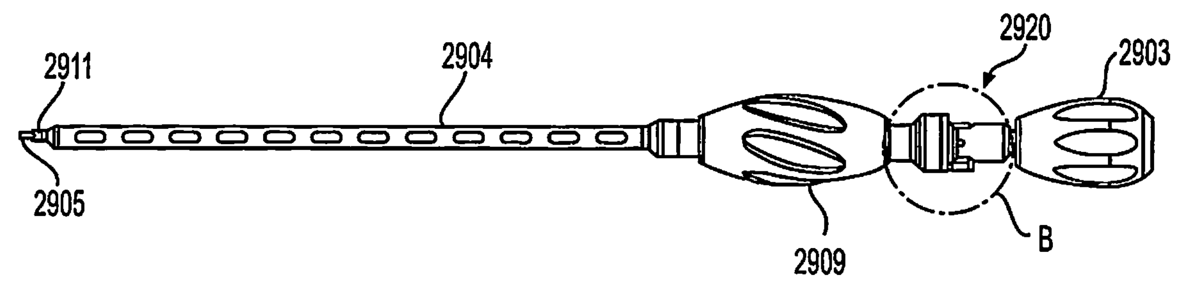
FIGS. 30A-30H depict the bi-directional driver of FIGS. 29A-29D in an assembled state.
Figure 30B:
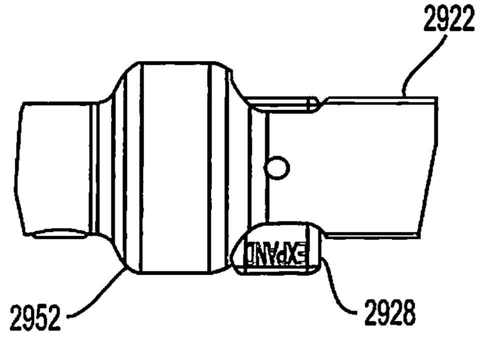
Figure 30C:
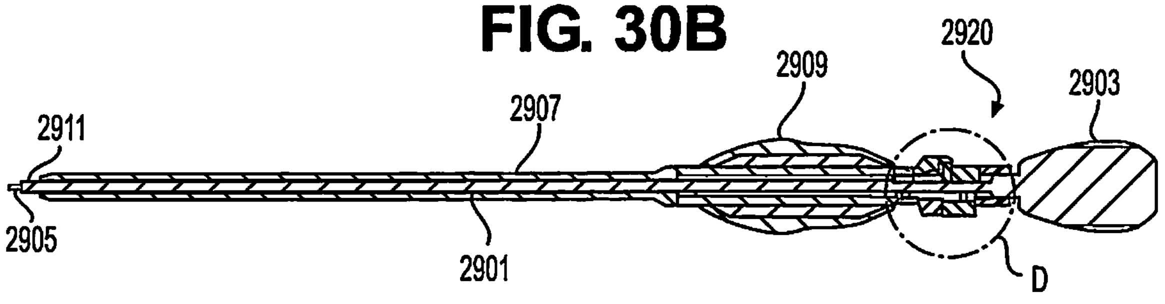
Figure 30D:
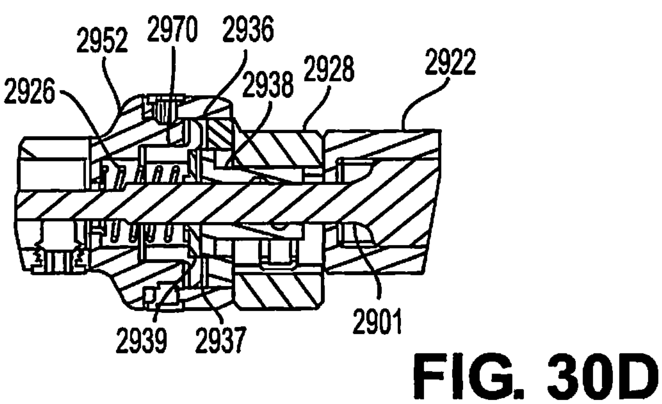
Figure 30E:
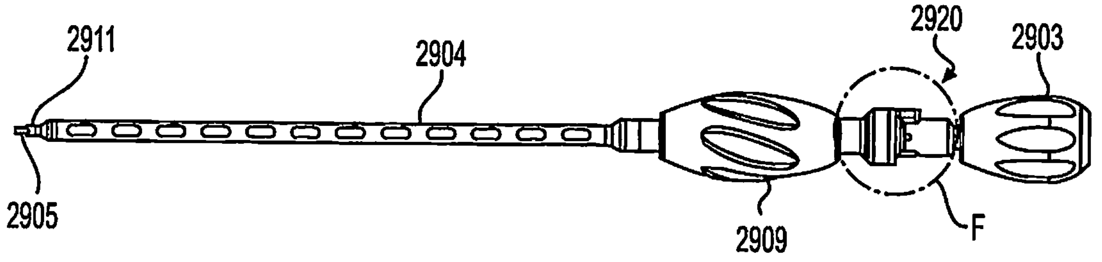
Figure 30F:
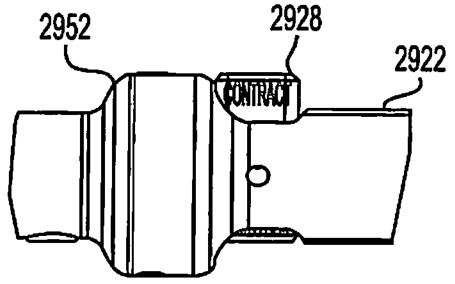
Figure 30G:
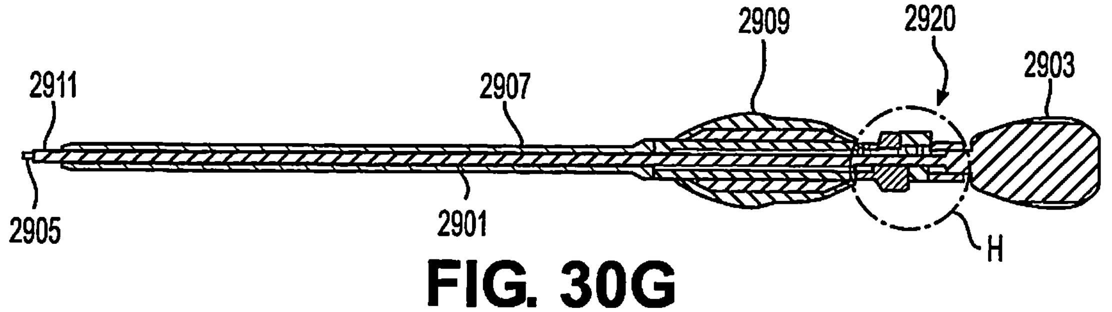
Figure 30H:
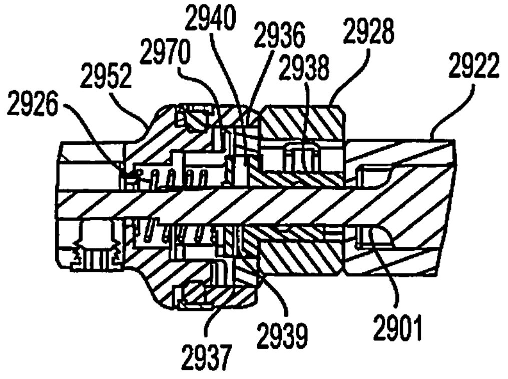

The resulting functionality is the allowance of relative rotation between the inner and outer drivers 2902, 2904 is allowed in a first direction when the outer ratcheting teeth ring 2936 engages the first set of ratcheting teeth 2937 (as shown in FIG. 30H). For example, the inner driver 2902 is allowed to rotate in a clockwise direction while the outer driver 2904 can be held still or rotated counterclockwise. However, both the inner and outer drivers 2902, 2904 can be rotated counterclockwise together (i.e., not independent of one another). Alternatively, when the ratcheting teeth 2940 of the ratchet pusher 2938 engage the second set of ratcheting teeth 2939 (as shown in FIG. 30D), relative rotation between the inner and outer drivers 2902, 2904 is allowed in a second direction. For example, the inner driver 2902 is allowed to rotate in a counterclockwise direction while the outer driver 2904 can be held still or rotated clockwise. However, both the inner and outer drivers 2902, 2904 can be rotated clockwise together (i.e., not independent of one another).

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A bi-directional driver, comprising:

an inner driver extending from a proximal end to a distal end, wherein the inner driver comprises:

a handle disposed at the proximal end of the inner driver;

an inner driver tip disposed at the distal end of the inner driver; and a shaft extending from the handle to the inner driver tip;

an outer driver extending from a proximal end to a distal end, wherein the outer driver comprises:

a handle portion disposed at the proximal end of the outer driver;

an outer driver tip disposed at the distal end of the outer driver; and a tubular shaft extending from the handle portion to the outer driver tip; and a rotational constraint system which couples the inner and outer drivers, the rotational constraint system configured to releasably prevent relative rotation between the inner and outer drivers and comprising a locking sleeve coupled to the shaft of the inner driver via a fixation element proximate the handle, a distal end of the locking sleeve having a first plurality of ratcheting teeth configured to mesh with and engage a first set of ratcheting teeth on the proximal end of the outer driver, wherein the locking sleeve includes an opening.

2. The bi-directional driver of claim 1, wherein the rotational constraint system comprises:

a push button extending through the opening of the locking sleeve and moveable between a first position and a second position, wherein the first position causes the rotational constraint system to be in the first configuration and the second position causes the rotational constraint system to be in the second configuration; and a ratchet pusher extending through the push button, wherein the ratchet pusher includes a second plurality of ratcheting teeth at a distal end of the ratchet pusher, wherein the second plurality of ratcheting teeth is configured to mesh with and engage a second set of ratcheting teeth on the proximal end of the outer driver, and wherein the second plurality of ratcheting teeth are oriented in an opposite direction as the first plurality of ratcheting teeth.

3. The bi-directional driver of claim 2, wherein the push button comprises one or more leaf spring elements configured to interface with edges of the opening of the locking sleeve such that the push button is captured at either side of a stroke of the push button.

4. The bi-directional driver of claim 1, wherein the first plurality of ratcheting teeth engages the first set of ratcheting teeth in the first configuration and the second plurality of ratcheting teeth engages the second set of ratcheting teeth in the second configuration.

5. The bi-directional driver of claim 4, wherein the second plurality of ratcheting teeth is disposed coaxial to and radially inward of the first plurality of ratchet teeth, and wherein the second set of ratcheting teeth is concentric to and radially inward of the first set of ratcheting teeth.

6. The bi-directional driver of claim 5, wherein the second plurality of ratcheting teeth are oriented in a direction opposite a direction of the first plurality of ratcheting teeth, and wherein the second set of ratcheting teeth are oriented in a direction opposite a direction of the first set of ratcheting teeth.

7. The bi-directional driver of claim 1, wherein an interior of the locking sleeve and a portion of the shaft that extends through the locking sleeve comprise mating flat surfaces to prevent the relative rotation of the locking sleeve with respect to the shaft.

8. The bi-directional driver of claim 1, further comprising:

a biasing element having an inwardly extending wall and being disposed within the locking sleeve, wherein the biasing element extends between the handle of the inner driver and the inwardly extending wall to bias the first plurality of ratcheting teeth of the locking sleeve into engagement with the first set of ratcheting teeth of the outer driver.

9. The bi-directional driver of claim 8, wherein the biasing element is a helical spring.

10. The bi-directional driver of claim 1, wherein the bi-directional driver is configured to expand or contract an implant for therapeutically separating bones of a joint.

11. A bi-directional driver, comprising:

an inner driver extending from a proximal end to a distal end and including a shaft;

an outer driver extending from a proximal end to a distal end; and a rotational constraint system which couples the inner and outer drivers, wherein the rotational constraint system is configured to prevent relative rotation between the inner and outer drivers in a first direction when the rotational constraint system is in a first configuration and in a second direction when the rotational constraint system is in a second configuration, and the rotational constraint system comprises a locking sleeve coupled to the shaft of the inner driver via a fixation element proximate the handle, a distal end of the locking sleeve having a first plurality of ratcheting teeth configured to mesh with and engage a first set of ratcheting teeth on the proximal end of the outer driver, wherein the locking sleeve includes an opening.

12. The bi-directional driver of claim 11, wherein the rotational constraint system comprises:

a push button extending through the opening of the locking sleeve and moveable between a first position and a second position, wherein the first position causes the rotational constraint system to be in the first configuration and the second position causes the rotational constraint system to be in the second configuration; and a ratchet pusher extending through the push button, wherein the ratchet pusher includes a second plurality of ratcheting teeth at a distal end of the ratchet pusher, wherein the second plurality of ratcheting teeth is configured to mesh with and engage a second set of ratcheting teeth on the proximal end of the outer driver, and wherein the second plurality of ratcheting teeth are oriented in an opposite direction as the first plurality of ratcheting teeth.

13. The bi-directional driver of claim 12, wherein the push button comprises one or more leaf spring elements configured to interface with edges of the opening of the locking sleeve such that the push button is captured at either side of a stroke of the push button.

14. The bi-directional driver of claim 12, wherein the first plurality of ratcheting teeth engages the first set of ratcheting teeth in the first configuration and the second plurality of ratcheting teeth engages the second set of ratcheting teeth in the second configuration.

15. The bi-directional driver of claim 14, wherein the second plurality of ratcheting teeth is disposed coaxial to and radially inward of the first plurality of ratchet teeth, and wherein the second set of ratcheting teeth is concentric to and radially inward of the first set of ratcheting teeth.

16. The bi-directional driver of claim 15, wherein the second plurality of ratcheting teeth are oriented in a direction opposite a direction of the first plurality of ratcheting teeth, and wherein the second set of ratcheting teeth are oriented in a direction opposite a direction of the first set of ratcheting teeth.

17. The bi-directional driver of claim 12, further comprising:

a biasing element having an inwardly extending wall and being disposed within the locking sleeve, wherein the biasing element extends between the handle of the inner driver and the inwardly extending wall to bias the first plurality of ratcheting teeth of the locking sleeve into engagement with the first set of ratcheting teeth of the outer driver.

18. The bi-directional driver of claim 17, wherein the biasing element is a helical spring.

19. The bi-directional driver of claim 11, wherein an interior of the locking sleeve and a portion of the shaft that extends through the locking sleeve comprise mating flat surfaces to prevent the relative rotation of the locking sleeve with respect to the shaft.

20. The bi-directional driver of claim 11, wherein the bi-directional driver is configured to expand or contract an implant for therapeutically separating bones of a joint.

* * * * *